(12) United States Patent
Anger et al.

(10) Patent No.: US 6,384,014 B1
(45) Date of Patent: *May 7, 2002

(54) PURIFIED FORM OF STREPTOGRAMINES, PREPARATION OF SAME AND PHARMACEUTICAL COMPOSITIONS CONTAINING THEM

(75) Inventors: Pascal Anger, Verrieres-le-Buisson; Jean-Claude Barriere, Bures-sur-Yvette; Bertrand Bonnavaud, Viroflay; Patrick Lefevre, Vincennes; Jean-Marc Paris, Vaires-sur-Marne; Denis Thibaut, Paris, all of (FR)

(73) Assignee: Aventis Pharma S.A., Antony Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/522,949

(22) Filed: Mar. 10, 2000

Related U.S. Application Data

(63) Continuation of application No. 08/776,546, filed as application No. PCT/FR95/01026 on Jul. 31, 1995.

(30) Foreign Application Priority Data

Aug. 2, 1994 (FR) .............................. 94 09564

(51) Int. Cl.[7] ..................... A61K 38/12; A61P 31/04; C07K 7/64
(52) U.S. Cl. .................. 514/11; 530/317; 530/344; 540/455
(58) Field of Search ............ 514/11; 540/455; 530/317, 344

(56) References Cited

U.S. PATENT DOCUMENTS 4,617,290 A  10/1986  Corbet et al. ............ 530/317

(List continued on next page.)

FOREIGN PATENT DOCUMENTS

| EP | A0 0 506 561 | 9/1992 |
| EP | 0 614 910 | 9/1994 |
| FR | 2619008 | 2/1989 |
| GB | 2275269 | 8/1994 |

OTHER PUBLICATIONS

Blanc, Molecular Microbiology, 23(2), 191, 1997.*

(List continued on next page.)

Primary Examiner—Mark L. Berch
(74) Attorney, Agent, or Firm—Finnegan, Henderson, Farabow, Garrett & Dunner, L.L.P.

(57) ABSTRACT

Purified form of streptogramines, characterised in that it contains at least one component from group B streptogramines of general formula (I), wherein $R_1$ is Me or Et, $R_2$ is H or OH, and $R_3$ is substituted benzyl of general formula (III), such that 1) if $R_2$ is H, R is $NR_4R_5$, wherein one of $R_4$ and $R_5$ is H or an Me radical and the other is Me, and R' is Cl or Br, or R is (C3–5)alkenyl if $R_4$ and $R_5$ are Me, or 2) R is H and R' is halogen, alkylamino or dialkylamino, an ether-oxide residue, alkylthio, (C1–3)alkyl or trihalogenomethyl, or R is halogen, (C2–4)alkylamino, (C2–4)dialkylamino or methyl ethyl amino, pyrrolidino alkenyl alkyl amino, dialkylamino, an alkyl cycloalkylmethyl amino radical or in ether-oxide residue, alkylthio, alkylthiomethyl, (C1–6)alkyl, aryl or trihalogenomethyl, and R' is H, or R is halogen, amino, alkylamino or dialkylamino, an ether-oxide residue, an alkylthio radical, (C1–6)alkyl or trihalogenomethyl and R' is halogen, alkylamino or dialkylamino, an ether-oxide residue or alkylthio, (C1–3)alkyl, cocrystallised with one or more minor components of group A of general formula (II) wherein R" is H, Me or Et.

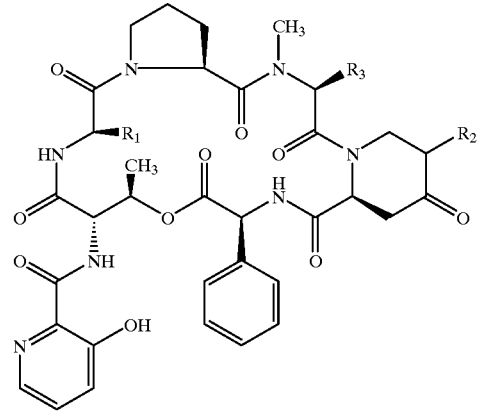

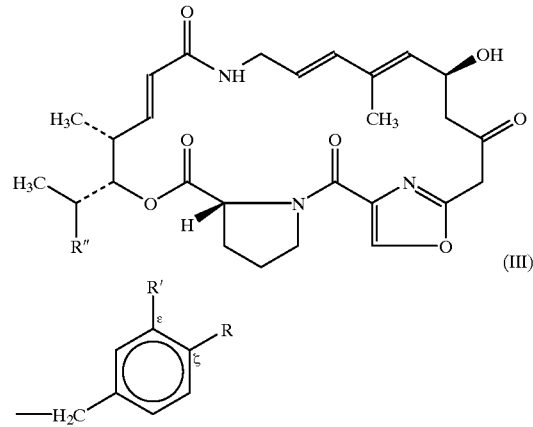

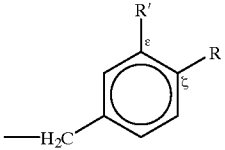

7 Claims, No Drawings

U.S. PATENT DOCUMENTS

| | | | |
|---|---|---|---|
| 4,618,599 A | 10/1986 | Corbet et al. | 530/317 |
| 4,668,669 A | 5/1987 | Barriere et al. | 530/317 |
| 4,798,827 A | 1/1989 | Barriere et al. | 530/317 |
| 5,637,565 A | 6/1997 | Anger et al. | 514/11 |
| 5,726,151 A | 3/1998 | Anger | 514/11 |
| 5,891,695 A | 4/1999 | Blanc | 435/183 |

OTHER PUBLICATIONS

Chabbert, Path.–Biol., vol. 19, pp. 613–619, 1971.

Sharma et al., Chemical Abstract No. 110(7):56082.

English language Derwent Abstract of EP A 0 506 561.

Preud'Homme et al., "Pristinamycine Isolement, Caractérisation et Identification des Constituants," Bulletin de la Societe Chimique de France, No. 2, pp. 585–591.

Certified English Translation of above listed by Preud'Homme et al., "Pristinamycin: Isolation, Characterization and Identification of the Constituents".

English Translation of FR A2,619,008.

* cited by examiner

PURIFIED FORM OF STREPTOGRAMINES, PREPARATION OF SAME AND PHARMACEUTICAL COMPOSITIONS CONTAINING THEM

This is a continuation of application Ser. No. 08/776,546, ABN filed Jan. 31, 1997, which is a U.S. National Phase application of PCT/FR95/01026, filed Jul. 31, 1995, all of which are incorporated herein by reference.

The present invention relates to a purified form of streptogramins comprising at least one component of the streptogramin B group defined below by the general formula (I) co-crystallized with at least one "minor" component of the A group defined below by the general formula (II).

Among the known streptogramins, pristinamycin (RP 7293), an antibacterial product of natural origin produced by *Streptomyces pristinaespiralis* was isolated for the first time in 1955. The pristinamycin marketed under the name of Pyostacin® consists mainly of pristinamycin IA and pristinamycin IIA.

Another antibacterial agent of the streptogramin class: virginiamycin, was prepared from *Streptomyces virginiae*, ATCC 13161 [Antibiotics and Chemotherapy, 5, 632 (1955)]. Virginiamycin (Staphylomycin®) consists mainly of factor S and factor $M_1$.

U.S. Pat. No. 3,325,359 describes pharmaceutical compositions comprising antibiotic substances constituting the antibiotic 899: factor S and factor M1.

Antibacterial agents of natural origin, of the streptogramin class, consist of a mixture of 2 groups of components: components of the B group and components of the A group, each group having its own particular antibacterial activity. It has been demonstrated that the combination formed by the 2 groups of components gives rise to a synergism of action which results in increased bacteriostatic and bactericidal activity and in broadening of the spectrum of activity.

Components of the streptogramin A and B groups have been described in Streptogramine als Modelsysteme für den Kationentransport durch Membranen, Dissertation zur Erlangung des Doktorgrades der Mathematisch-Naturwissenschaftlichen Facultät der Georg-August Universität zu Göttingen, Göttingen 1979, in Antibiotics III, 521 (1975) and in Antibiotics of the virginiamycin family, Inhibitors which contain synergistic components, C. Cocito, Microbiological Reviews, 145–98 (1979). J. Preud'Homme, P. Tarridec, and A. Belloc, Bull. Soc. Chim. Fr., 2, 585 (1968) have also described natural pristinamycin as well as the various components constituting it.

As regards the industrial preparation of products of this class, the techniques available hitherto did not make it possible to obtain, on a preparative scale, a sufficiently purified form and the production of batches of sufficiently constant and reproducible quality to meet the requirements of the registration legislations in certain countries.

In the field of antibacterial agents, it is well known by practitioners that allergies or resistances may develop after administration of certain classes of antibiotics [The New England Journal of Medicine, 324 (9), 601 (1991)]. In hospitals, many resistant strains of *Staphylococcus aureus* are known in particular. Accordingly, it is extremely useful for doctors to have at their disposal a wide range of chemically different classes so as to be able to adapt the treatment to the specific case of the patient to be treated. The consequence of the absence of commercialization of a given class may be very serious, or even dramatic, since the result can be that patients who do not tolerate the other classes of antibiotics are deprived of treatment.

Thus, the purification tests used always had the aim of removing the minor components from streptogramins, these components being considered as not indispensable and rather as impurities.

Among the components of the A group of natural streptogramins, pristinamycin IIB (PIIB) is a minor component whose weight proportion is less than 10% in natural pristinamycin, and usually about 8% or even about 6% in virginiamycin.

It has now been found, and this forms the subject of the present invention, that the combination consisting of one or more components of the B group, of general formula:

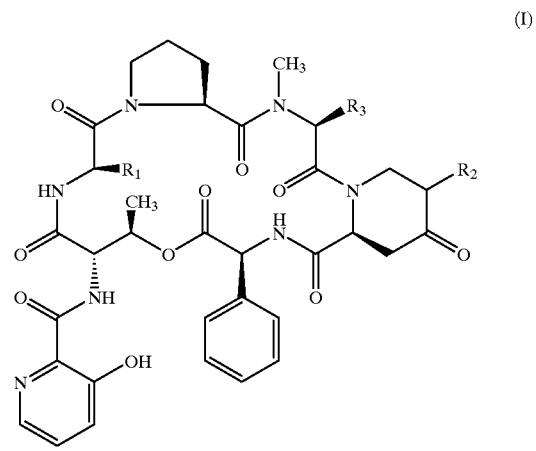

(I)

in which the symbol $R_1$ represents a methyl or ethyl radical, the symbol $R_2$ represents a hydrogen atom or a hydroxyl radical, and the symbol $R_3$ represents a substituted benzyl radical of general formula:

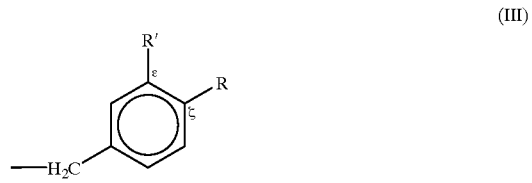

(III)

in which 1) on the condition that $R_2$ is simultaneously hydrogen, R represents $NR_4R_5$ for which one of the symbols $R_4$ and $R_5$ is a hydrogen atom or a methyl radical and the other is a methyl radical and R' is a chlorine or bromine atom, or represents an alkenyl radical containing 3 to 5 carbon atoms if $R_4$ and $R_5$ are methyl radicals, or alternatively 2) R is a hydrogen atom and R' represents a halogen atom, an alkylamino or dialkylamino radical, an ether oxide residue, an alkylthio radical, an alkyl radical containing 1 to 3 carbon atoms in a straight or branched chain or a trihalomethyl radical, or alternatively R is a halogen atom, an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an alkenylalkylamino radical in which the alkenyl part contains 3 or 4 carbon atoms and the alkyl part is defined as above, a dialkylamino radical in which the alkenyl parts are defined as above, an alkylcycloalkylmethylamino radical in which the alkyl part is defined as above and the cycloalkyl part contains 3 or 4 carbon atoms, an ether oxide residue, an alkylthio radical, an alkylthiomethyl radical, an alkyl radical containing 1 to 6 carbon atoms in a straight or branched chain, an aryl radical or a trihalomethyl radical, and R' is a hydrogen atom, or alternatively R is a halogen atom, an amino, alkylamino or dialkylamino radical, an ether oxide residue, an alkylthio radical, an alkyl radical containing 1 to 6 carbon atoms in a straight or branched chain or a trihalomethyl radical and R' represents a halogen atom, an alkylamino or dialkylamino radical, an ether oxide residue or an alkylthio or alkyl radical containing 1 to 3 carbon atoms in a straight or branched chain, and one or more "minor" components of the streptogramin A group, of general formula:

(II)

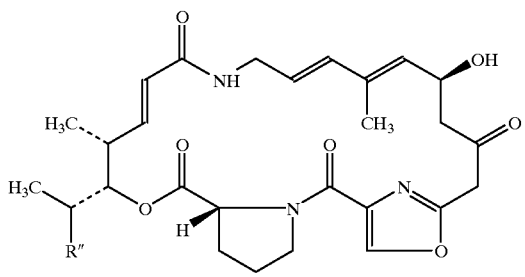

in which R" is a hydrogen atom or a methyl or ethyl radical, is particularly advantageous on account of its in vivo biological activity.

In the general formula (I), when R or R' (in $R_3$) represents a halogen atom, it is preferably a fluorine atom, except for if R' is a hydrogen atom, in which case R is either chlorine, bromine, fluorine or iodine; when R' represents an alkylamino or dialkylamino radical, the alkyl radicals are preferably chosen from methyl and ethyl; when R or R' represents is an ether oxide residue, it may be represented by a residue OR° for which R° is preferably chosen from a methyl group, an ethyl group optionally substituted with a chlorine atom, an allyl group or a trifluoromethyl group; when R or R' represents an alkylthio radical, it is preferably a methylthio radical; when R represents an alkyl radical containing 1 to 6 carbon atoms, it preferably represents methyl, isopropyl or tert-butyl; when R represents an aryl radical, it is preferably a phenyl radical; when R or R' represents a trihalomethyl radical, it is preferably a trifluoromethyl radical. Moreover, it is understood that, except where especially mentioned, the alkyl radicals are straight or branched and contain 1 to 4 carbon atoms.

The product of general formula (II) for which R" is an ethyl radical, referred to hereinbelow as pristinamycin IIF (PIIF), and the product of general formula (II) for which R" is a hydrogen atom, referred to hereinbelow as pristinamycin IIG (PIIG), are products which constitute very minor components of streptogramins, the weight proportion of which components is less than 0.5% in batches of natural product.

The co-crystallization is carried out at a constant stoichiometry of 1 mol of component(s) of general formula (I) with 2 mol of component(s) of the A group of general formula (II) [this stoichiometry corresponding to a relative proportion of about 43–49/57–51 by weight].

According to the invention, the co-crystallized combinations are prepared in the following way: a component of the B group defined by the general formula (I) is added to a crude mixture containing at least 30% of a minor component of the A group corresponding to the general formula (II) dissolved in an organic solvent such as a ketone (acetone, methyl ethyl ketone or methyl isobutyl ketone for example), an ester (ethyl acetate, isopropyl acetate, butyl acetate or isobutyl acetate for example), a chlorinated solvent (methylene chloride, chloroform or 1,2-dichloroethane for example) or a nitrile (acetonitrile for example) to give a co-crystallized compound in the proportions defined above. It is understood that the amount of compound of general formula (I) introduced is conveniently chosen so that the residual concentration of this product (after the co-crystallization) is less than its solubility in the medium. It is also understood that variations in the respective contents of product of general formula (II) and of product of general formula (I) in the initial medium do not lead to any change in the co-crystallized compound obtained.

This co-crystallized combination has the advantage of very good stability and high purity.

The components of the B group of the streptogramins defined by the general formula (I) may be prepared in the following way:

When $R_3$ represents a radical of general formula (III) for which R and R' are defined as. in 1), if R' is a chlorine or bromine atom, the products of general formula (I) may be obtained by the action of the corresponding N-halosuccinimide derivative on pristinamycin I for which R' is a hydrogen atom.

The reaction is carried out using N-chloro- or N-bromosuccinimide in an organic solvent such as, for example, a chlorinated solvent (dichloromethane, dichloroethane or chloroform) or a nitrile (acetonitrile), at a temperature of between 20 and 80° C.

When $R_3$ represents a radical of general formula (III) for which R and R' are defined as in 1), if R' is an alkenyl radical containing 3 to 5 carbon atoms, the products of general formula (I) may be obtained by rearrangement, in a slightly basic medium, of a salt derived from 4-N-alkenylammoniopristinamycin IA of general formula:

(IV)

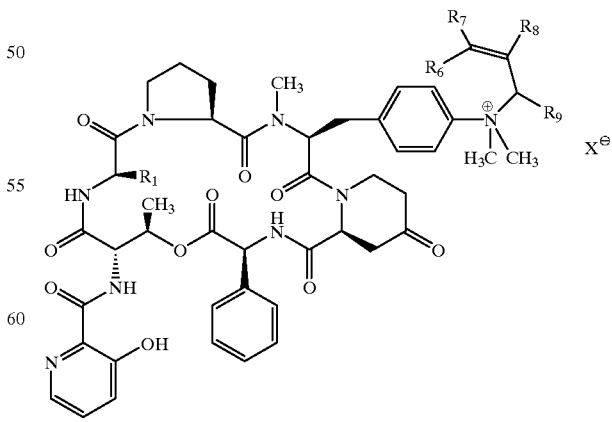

in which $R_1$ is defined as above and $R_6$, $R_7$, $R_8$ and $R_9$ are a hydrogen atom or a methyl radical, provided that at least 2 of them are hydrogen atoms and X⁻ represents an anion, to give the derivative of general formula:

(V)

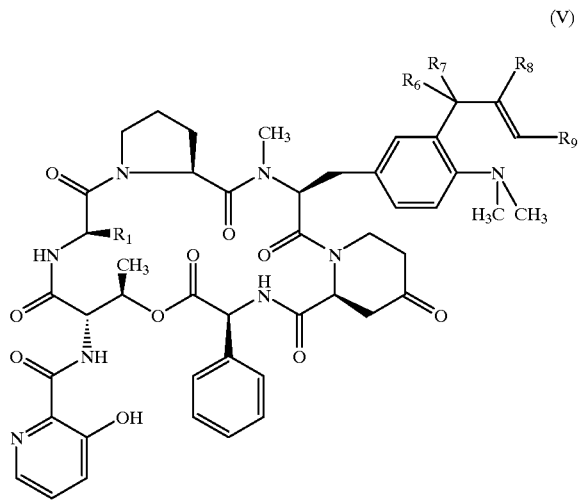

for which $R_1$, $R_6$, $R_7$, $R_8$ and $R_9$ are defined as above.

The reaction is carried out by heating at a temperature of between 80 and 100° C. in an aqueous or two-phase medium (for example in ethyl acetate/water medium), in the presence of sodium acetate or sodium or potassium bicarbonate. A 4-N-alkenylammoniopristinamycin IA halide is advantageously used.

The 4-N-alkenylammoniopristinamycin IA halide may be obtained by the action of an alkenyl halide of general formula:

(VI)

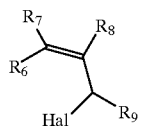

for which $R_6$, $R_7$, $R_8$ and $R_9$ are defined as above and Hal represents a halogen atom, on a pristinamycin derivative of general formula:

(VII)

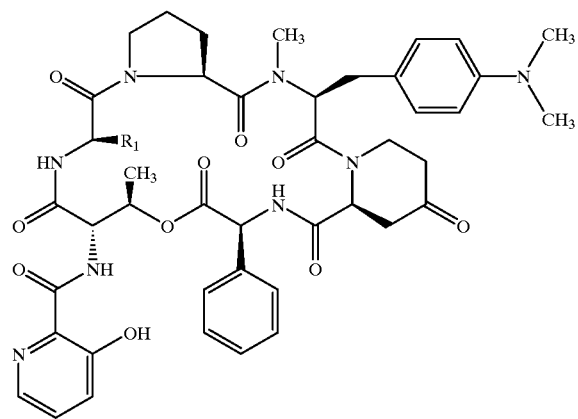

in which $R_1$ is defined as above.

The reaction is advantageously carried out in an organic solvent such as a chlorinated solvent (for example dichloromethane, dichloroethane or chloroform) or an alcohol (for example ethanol) or in a mixture, at a temperature of between 20° C. and the reflux temperature of the reaction mixture. Preferably, a product of general formula (VI) for which Hal is a chlorine or bromine atom is reacted.

When $R_3$ represents a radical of general formula (III) for which R and R' are defined as in 2), the products of general formula (I) may be obtained as described below in the examples, from a strain of a streptogramin-producing microorganism possessing at least one genetic modification which affects the biosynthesis of a precursor of the group B streptogramins, the said mutant strain cultured in a suitable culture medium, complemented with at least one original precursor other than that whose biosynthesis is adversely affected (and corresponding to the desired structure), produces the expected streptogramin derivatives.

The strains used in the context of the present invention are thus mutated strains producing natural streptogramins (pristinamycin IA, pristinamycin IB and virginiamycin S). The said genetic modification(s) may be localized either onto one of the genes involved in the biosynthesis of the said precursors or outside of the coding region, for example in regions responsible for the transcriptional or post-transcriptional regulation and/or expression of the said genes or in a region belonging to the transcript containing the said genes.

In particular, the mutant strains possess one or more genetic modifications in at least one of their genes involved in the biosynthesis of precursors of the group B streptogramins. This or these genetic modifications adversely affect the expression of the said gene, that is to say make this gene and, where appropriate, another of the genes involved in the biosynthesis of the precursors partially or totally incapable of coding for the natural enzyme involved in the biosynthesis of at least one precursor.

The genes liable to be mutated are preferably the genes involved in the biosynthesis of the precursor 4-dimethylamino-L-phenylalanine (DMPAPA). These are preferably the genes papA, papM, papB (SEQ ID No. 3) and papC (SEQ ID No. 2). The genes papA and papM have already been described in patent application PCT/FR93/0923.

By complementing the culture medium of mutant strains according to the invention with at least one original precursor, it turns out to be possible to orient the biosynthesis towards the novel streptogramins of general formula (I).

The precursors used in the context of the present invention are phenylalanine derivatives as well as a-ketocarboxylic acid derivatives which may be represented by the general formula:

(VIII)

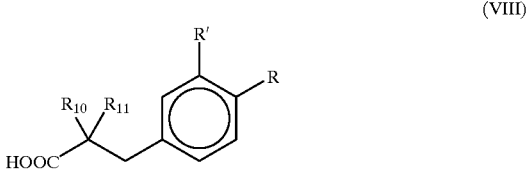

in which R and R' are defined as above in 2) and $R_{10}$ is a hydrogen atom and $R_{11}$ is an amino radical, or alternatively $R_{10}$ and $R_{11}$ together form an oxo radical.

As precursors which are suitable for the invention, mention may be made in particular of the following:
4-diethylaminophenylalanine, 4-ethylaminophenylalanine, 4-methylthiophenylalanine, 4-methylphenylalanine, 4-methoxyphenylalanine, 4-trifluoromethoxyphenyl-
alanine,
4-chlorophenylalanine, 4-bromophenylalanine,
4-iodophenylalanine, 4-trifluoromethylphenylalanine,
4-tert-butylphenylalanine, 4-isopropylphenylalanine,
3-methylaminophenylalanine, 3-methoxyphenylalanine,
3-methylthiophenylalanine, 3-fluorophenylalanine,
4-tert-butylphenylpyruvic acid, 4-fluorophenylalanine,
3-ethoxyphenylalanine, 3,4-dimethylphenylalanine,
3-methylphenylalanine, 4-butylphenylalanine,
3-trifluoromethylphenylalanine and 3-ethylamino-
phenylalanine, 4-aminomethylphenylalanine.

The preparation and separation of the components of the natural streptogramins of groups A [streptogramins of general formula (II)] and B [and in particular the products of general formula (VII)] are carried out by fermentation and isolation of the constituents from the fermentation broth according to or by analogy with the method described by J. Preud'homme et al., Bull. Soc. Chim. Fr., vol. 2, 585 (1968) in Antibiot. & Chemother., 5, 632 (1955) or 7, 606 (1957), in Chromatog. Sym., 2° Bruxelles, 181 (1962), in Antibiot. Ann., 728 784 (1954–55), in U.S. Pat. No. 3,299,047 or in Streptogramine als Modelsysteme für den Kationentransport durch Membranen, Dissertation zur Erlangung des Doktorgrades der Mathematisch-Naturwissenschaftlichen Facultät der Georg-August Universität zu Göttingen, Göttingen 1979, or as described below in the examples. In particular, in the case of pristinamycins, the components of the A and B groups are separated by suspending the crude streptogramin in an organic solvent such as an acetate (for example ethyl acetate), followed by filtration or centrifugation of the crude component of the A group and extraction of the component of the B group in aqueous acidic medium, followed by a re-extraction in chloromethylenic medium. The components of the A and B groups may also be separated by acidic extraction of a solution of crude streptogramin in methyl isobutyl ketone, followed by isolation by extraction of the component of the B group from the aqueous phase and isolation of the component of the A group by precipitation from the organic phase.

After separation, the components of the streptogramin B group may be purified by crystallization from an alcohol such as ethanol, methanol or isopropanol, from an acetate (for example isopropyl acetate or butyl acetate), from a ketone (for example methyl ethyl ketone) or from acetonitrile, or by chromatography. The components of the A group of general formula (II) may be purified by chromatography, eluting with an acetonitrile/water mixture.

Alternatively, the natural components of the A and B groups respectively of general formula (II) and in particular of general formula (VII) are prepared as described in French patent application 2,689,518, by separate fermentation.

Thus, according to the invention, it is now possible to obtain a novel purified and crystallized form of streptogramin in which the level of impurities, the definition and the constancy of the composition are improved and which moreover possesses improved in vivo activity and low toxicity. The novel co-crystallized combination will thus be able to overcome the absence of treatment by an antibacterial agent of this class in many countries.

The combinations according to the invention exhibit an in vivo biological action which is superior to that of the streptogramin combinations known hitherto, in the form of a mixture of powders.

The novel co-crystallized combination of a component of the streptogramin B group of general formula (I) and a component of the streptogramin A i group of general formula (II) is of particularly advantageous in vivo activity, in particular on Gram-positive microorganisms. In vivo, in mice, it proved to be active on *Staphylococcus aureus* IP 8203 at doses of from 25 to 50 mg/kg via the oral route.

Furthermore, the novel combination has no toxicity: no sign of toxicity is exhibited in mice at a dose of 150 mg/kg via the oral route (2 administrations).

The co-crystallized combination according to the invention may also be used as a means of purifying a minor component of streptogramins corresponding to the general formula (II).

Indeed, it has never been possible to purify a component of the A group of general formula (II) by crystallization.

It has now been shown that the component of the A group of general formula (II) can be-obtained in the pure state via the intermediate co-crystallized combination defined above.

According to the invention, when the co-crystallized combination is used as a means of purifying the component of general formula (II), the latter may be obtained by acidic extraction of a solution of the co-crystallized compound in a ketone (for example methyl isobutyl ketone), followed by isolation of the component of the A group by precipitation from the organic phase, when R or R' represents alkylamino or dialkylamino; or alternatively by high performance liquid chromatography.

Of particular interest are co-crystallized combinations which comprise at least one component of the streptogramin B group defined by the general formula (I), in which the symbols $R_1$ and $R_2$ are defined as above, and the symbol $R_3$ represents a substituted benzyl radical of general formula (III) in which 1) on condition that $R_2$ is simultaneously hydrogen, R represents $NR_4R_5$ for which one of the symbols $R_4$ and $R_5$ is a hydrogen atom or a methyl radical and the other is a methyl radical and R' is a chlorine or bromine atom, or represents an alkenyl radical containing 3 to 5 carbon atoms if $R_4$ and $R_5$ are methyl radicals, or alternatively 2) R is a hydrogen atom and R' represents an alkylamino or dialkylamino radical, an ether oxide residue or an alkylthio radical, or alternatively R is an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an alkenylalkylamino radical in which the alkenyl part contains 3 or 4 carbon atoms and the alkyl part is defined as above, an ether oxide residue, an alkylthio radical, an alkyl radical containing 1 to 6 carbon atoms in a straight or branched chain or a trihalomethyl radical, and R' is a hydrogen atom, or alternatively R is an alkyl radical containing 1 to 6 carbon atoms in a straight or branched chain and R' represents a halogen atom, co-crystallized with at least one "minor" component of the streptogramin A group as defined above, it being understood that, except where specially mentioned, the alkyl radicals are straight or branched and contain 1 to 4 carbon atoms.

Among these products, the preferred combinations are co-crystallized combinations which comprise at least one component of the streptogramin B group defined by the general formula (I), in which the symbol $R_1$ is an ethyl radical, the symbol $R_2$ is a hydrogen atom, and the symbol $R_3$ represents a substituted benzyl radical of general formula (III) in which:

1) on condition that $R_2$ is simultaneously hydrogen, R represents $NR_4R_5$ for which one of the symbols $R_4$ and $R_5$ is a hydrogen atom or a methyl radical and the other is a methyl radical and R' is a chlorine or bromine atom, or represents an allyl radical if $R_4$ and $R_5$ are methyl radicals, or alternatively 2) R is a hydrogen atom and R' represents an alkylamino or dialkylamino radical, a methoxy, ethoxy, allyloxy or trifluoromethoxy radical or an alkylthio radical, or alternatively R is an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an allylalkylamino radical in which the alkyl part is defined as above, a methoxy, ethoxy, allyloxy or trifluoromethoxy radical, an alkylthio radical, an alkyl radical containing 1 to 6 carbon atoms in a straight or branched chain or a trifluoromethyl radical, and R' is a hydrogen atom, or alternatively R is an alkyl radical containing 1 to 6 carbon atoms in a straight or branched chain and R' represents a halogen atom, co-crystallized with at least one "minor" component of the streptogramin A group as defined above, it being understood that, except where specially mentioned, the alkyl radicals are straight or branched and contain 1 to 4 carbon atoms.

The examples which follow, given without any limitation being implied, illustrate the present invention.

In the examples which follow, it is understood that the titres are given as a % by weight. The analytical chromatographies (HPLC) were performed in isocratic mode at 0.8 ml/min with an eluent composed of 40% acetonitrile and 60% 0.1 M phosphate buffer pH=2.9 on a 5µ Nucleosil 100 C8® column (4×133 mm, Macherey Nagel). The steptogramins are detected and assayed by their UV absorbance at 206 am. The titres presented have been normalized to 100%. The X-ray diffraction diagrams were produced on a Phillips PW1700® diffractometer with a cobalt anticathode. The reference 100 is given for the line at 15.8 Å. The relative values are estimated by measuring the height of the line, with the continuous background subtracted. In the examples which follow, the X-ray diffraction spectrum of the co-crystallized product is different from the spectrum of the component of the B group crystallized only in the same solvent, when it exists in crystallized form.

PREPARATION OF A CO-CRYSTALLIZED PRODUCT

EXAMPLE 1

672 mg of 4-ε-bromopristinamycin $I_A$ are added to a solution of 784 mg of pristinamycin IIB in 7 cm³ acetone. After warming to facilitate dissolution and then returning to 20° C., precipitation is observed. After stirring for 20 hours at 20° C., the product is filtered off, washed with acetone and dried to constant weight under reduced pressure (135 Pa). 940 mg of the co-crystallized combination of 2 molecules of pristinamycin IIB and one molecule of 4-ε-bromopristinamycin $I_A$ are thus obtained in the form of white crystals melting at 188° C., giving a titre of about 53% pristinamycin IIB and 44% 4-ε-bromopristinamycin $I_A$.

X-ray Diffraction Diagram

The relative intensities of the main lines are given in the following table.

| Interplanar spacing (Å) | |
|---|---|
| 15.8 | 100 |
| 10.3 | 36 |
| 5.9 | 54 |
| 5.2 | 68 |
| 5.0 | 39 |

EXAMPLE 2

Working as described above in Example 1, but using 112 mg of pristinamycin IIB and 96 mg of 4-ε-chloropristinamycin $I_A$ in 1 cm³ of acetone, 130 mg of the co-crystallized combination of 2 molecules of pristinamycin IIB and one molecule of 4-ε-chloropristinamycin $I_A$ are obtained in the form of white crystals melting at 190° C., giving a titre of about 55% pristinamycin IIB and 45% 4-ε-chloropristinamycin $I_A$.

X-ray Diffraction Diagram

The relative intensities of the main lines are given in the following table.

| Interplanar spacing (Å) | |
|---|---|
| 15.8 | 100 |
| 10.3 | 55 |
| 5.9 | 43 |
| 5.2 | 71 |
| 5.0 | 47 |

EXAMPLE 3

Working as described above in Example 1, but using 112 mg of pristinamycin IIB and 96 mg of 4-ε-allylpristinamycin $I_A$ in 1 cm³ of acetone, 160 mg of the co-crystallized combination of 2 molecules of pristinamycin IIB and one molecule of 4-ε-allylpristinamycin $I_A$ are obtained in the form of white crystals melting at 182° C., giving a titre of about 53% pristinamycin IIB and 47% 4-ε-allylpristinamycin $I_A$.

X-ray Diffraction Diagram

The relative intensities of the main lines are given in the following table.

| Interplanar spacing (Å) | |
|---|---|
| 15.6 | 80 |
| 10.6 | 100 |
| 6.6 | 37 |
| 4.6 | 63 |

EXAMPLE 4

Working as described above in Example 1, but using 560 mg of pristinamycin IIB and 480 mg of 4-ε-bromopristinamycin $I_B$ in 5 cm³ of acetone, 730 mg of the co-crystallized combination of 2 molecules of pristinamycin IIB and one molecule of 4-ε-bromopristinamycin $I_B$ are obtained in the form of white crystals melting at 179° C., giving a titre of about 53% pristinamycin IIB and 47% 4-ε-bromopristinamycin $I_B$.

X-ray Diffraction Diagram

The relative intensities of the main lines are given in the following table.

| Interplanar spacing (Å) | |
|---|---|
| 15.8 | 100 |
| 10.3 | 47 |
| 5.9 | 53 |
| 5.2 | 66 |
| 5.0 | 39 |

EXAMPLE 5

Working as described above in Example 1, but using 784 mg of pristinamycin IIB and 672 mg of 4-ε-chloropristinamycin $I_B$ in 7 cm³ of acetone, 1.0 g of the co-crystallized combination of 2 molecules of pristinamycin IIB and one molecule of 4-ε-chloropristinamycin $I_B$ are obtained in the form of white crystals melting at 178° C., giving a titre of about 57% pristinamycin IIB and 43% 4-ε-chloropristinamycin $I_B$.

X-ray Diffraction Diagram

The relative intensities of the main lines are given in the following table.

| Interplanar spacing (Å) | |
|---|---|
| 15.8 | 100 |
| 10.3 | 62 |
| 5.9 | 43 |
| 5.2 | 60 |
| 5.0 | 43 |

EXAMPLE 6

Working as described above in Example 1, but using 425 mg of pristinamycin IIB and 364 mg of de(4-N-dimethylamino)-4-ζ-tert-butylpristinamycin $I_A$ in 3.8 cm³ of acetone, 305 mg of the co-crystallized combination of 2 molecules of pristinamycin IIB and one molecule of de(4-ζ-dimethylamino)-4-ζ-tert-butylpristinamycin $I_A$ are obtained in the form of white crystals melting at 170° C., giving a titre of about 57% pristinamycin IIB and 43% de(4-ζ-dimethylamino)-4-ζ-tert-butylpristinamycin $I_A$.

X-ray Diffraction Diagram

The relative intensities of the main lines are given in the following table.

| Interplanar spacing (Å) | |
|---|---|
| 15.8 | 100 |
| 10.3 | 68 |
| 5.9 | 39 |
| 5.2 | 66 |
| 5.0 | 46 |

EXAMPLE 7

Working as described above in Example 1, but using 168 mg of pristinamycin IIB and 144 mg of de(4-ζ-dimethylamino)-4-ζ-isopropylpristinamycin $I_A$ in 1.5 cm³ of acetone, 270 mg of the co-crystallized combination of 2 molecules of pristinamycin IIB and one molecule of de(4-ζ-dimethylamino)-4-ζ-isopropylpristinamycin $I_A$ are obtained in the form of white crystals melting at 180° C., giving a titre of about 56% pristinamycin IIB and 44% de(4-ζ-dimethylamino)-4-ζ-isopropylpristinamycin $I_A$.

X-ray Diffraction Diagram

The relative intensities of the main lines are given in the following table.

| Interplanar spacing (Å) | |
|---|---|
| 15.8 | 100 |
| 10.3 | 76 |
| 5.9 | 65 |
| 5.2 | 81 |
| 5.0 | 59 |

EXAMPLE 8

Working as described above in Example 1, but using 224 mg of pristinamycin IIB and 192 mg of de (4-N-dimethylamino)-4-ζ-methoxypristinamycin $I_A$ in 2 cm³ of acetone, 320 mg of the co-crystallized combination of 2 molecules of pristinamycin IIB and one molecule of de(4-ζ-dimethylamino)-4-ζ-methoxypristinamycin $I_A$ are obtained in the form of white crystals melting at 169° C., giving a titre of about 54% pristinamycin IIB and 46% de(4-ζ-dimethylamino)-4-ζ-methoxypristinamycin $I_A$.

X-ray Diffraction Diagram

The relative intensities of the main lines are given in the following table.

| Interplanar spacing (Å) | |
|---|---|
| 15.8 | 100 |
| 10.3 | 72 |
| 5.9 | 63 |
| 5.2 | 72 |
| 5.0 | 50 |

EXAMPLE 9

Working as described above in Example 1, but using 149 mg of pristinamycin IIB and 128 mg of de(4-N-dimethylamino)-4-ζ-methylpristinamycin $I_A$ in 1.3 cm³ of acetone, 205 mg of the co-crystallized combination of 2 molecules of pristinamycin IIB and one molecule of de(4-ζ-dimethylamino)-4-ζ-methylpristinamycin $I_A$ are obtained in the form of white crystals, giving a titre of about 56% pristinamycin IIB and 44% de(4-ζ-dimethylamino)-4-ζ-methylpristinamycin $I_A$.

EXAMPLE 10

A solution of 1.6 g of de(4-ζ-dimethylamino)-4-ζ-methylthiopristinamycin $I_A$ in 7 cm³ of acetone are added to a solution of 1.94 g of pristinamycin IIB in 6 cm³ of acetone. The mixture is stirred for 30 minutes and then filtered. The crystals obtained are rinsed with 5 times 1 cm³ of acetone, then with 3 times 10 cm³ of pentane and then dried to constant weight under reduced pressure (2.7 kPa). 2.3 g of the co-crystallized combination of 2 molecules of pristinamycin IIB and one molecule of de(4-ζ-dimethylamino)-4-ζ-methylthiopristinamycin $I_A$ are thus obtained in the form of white crystals melting at 183° C., giving a titre of about 51% pristinamycin IIB and 49% de(4-ζ-dimethylamino)-4-ζ-methylthiopristinamycin $I_A$.

X-ray Diffraction Diagram

The relative intensities of the main lines are given in the following table.

| Interplanar spacing (Å) | |
| --- | --- |
| 15.8 | 100 |
| 10.3 | 47 |
| 5.9 | 61 |
| 5.2 | 84 |
| 5.0 | 59 |

EXAMPLE 11

Working as described in Example 10, but using 106 mg of pristinamycin IIB and 86 mg of de(4-ζ-dimethylamino)-4-ε-methylaminopristinamycin $I_A$ and after stirring for 18 hours, 41 mg of the co-crystallized combination of 2 molecules of pristinamycin IIB and one molecule of de(4-ζ-dimethylamino)-4-ε-methylaminopristinamycin $I_A$ are obtained in the form of white crystals, giving a titre of about 53% pristinamycin IIB and 47% de(4-ζ-dimethylamino)-4-ε-methylaminopristinamycin $I_A$.

X-ray Diffraction Diagram

The relative intensities of the main lines are given in the following table.

| Interplanar spacing (Å) | |
| --- | --- |
| 15.8 | 100 |
| 10.3 | 31 |
| 5.9 | 31 |
| 5.2 | 41 |
| 5.0 | 30 |

EXAMPLE 12

Working as described in Example 10, but using 57 mg of pristinamycin IIB and 48 mg of de(4-ζ-dimethylamino)-4-ζ-trifluoromethylpristinamycin $I_A$ and after stirring for 17 hours, 62 mg of the co-crystallized combination of 2 molecules of pristinamycin IIB and one molecule of de(4-ζ-dimethylamino)-4-ζ-trifluoromethylpristinamycin $I_A$ are obtained in the form of white crystals melting at 183° C., giving a titre of about 55% pristinamycin IIB and 45% de(4-ζ-dimethylamino)-4-ζ-trifluoromethylpristinamycin $I_A$.

EXAMPLE 13

Working as described in example 10, but using 370 mg of pristinamycin IIB and 300 mg of de(4-ζ-dimethylamino)-4-ε-methoxypristinamycin $I_A$ and after stirring for 17 hours, 330 mg of the co-crystallized combination of 2 molecules of pristinamycin IIB and one molecule of de(4-ζ-dimethylamino)-4-ε-methoxypristinamycin $I_A$ are obtained in the form of white crystals melting at 180° C., giving a titre of about 48% pristinamycin IIB and 52% de(4-ζ-dimethylamino)-4-ε-methoxypristinamycin $I_a$.

X-ray Diffraction Diagram

The relative intensities of the main lines are given in the following table.

| Interplanar spacing (Å) | |
| --- | --- |
| 15.5 | 52 |
| 10.5 | 62 |
| 9.7 | 100 |
| 5.2 | 42 |
| 4.7 | 52 |

EXAMPLE 14

Working as described in Example 10, but using 70 mg of pristinamycin IIB and 75 mg of de(4-ζ-dimethylamino)-4-ε-fluoro-4-ζ-methylpristinamycin $I_A$ (with a titre of 75%) and after stirring for 3 hours 45 minutes, 57 mg of the co-crystallized combination of 2 molecules of pristinamycin IIB and one molecule of de(4-ζ-dimethylamino)-4-ε-fluoro-4-ζ-methylpristinamycin $I_A$ are obtained in the form of white crystals melting at 184° C., giving a titre of about 53% pristinamycin IIB and 47% de(4-ζ-dimethylamino)-4-ε-fluoro-ζ-methylpristinamycin $I_A$.

X-ray Diffraction Diagram

The relative intensities of the main lines are given in the following table.

| Interplanar spacing (Å) | |
| --- | --- |
| 15.8 | 100 |
| 10.3 | 71 |
| 5.9 | 54 |
| 5.2 | 88 |
| 5.0 | 50 |

EXAMPLE 15

Working as described above in Example 1, but using 61 mg of pristinamycin IIB and 50 mg of 4-ε-ethoxyde(4-ζ-dimethylamino)pristinamycin $I_A$ in 0.6 cm³ of acetone, 30 mg of the co-crystallized combination of 2 molecules of pristinamycin $I_A$ and one molecule of 4-ε-ethoxyde(4-ζ-dimethylamino)pristinamycin IIB are obtained in the form of white crystals melting at 182° C., giving a titre of 59% pristinamycin IIB and 41% 4-ε-ethoxyde(4-ζ-dimethylamino)pristinamycin $I_A$.

X-ray Diffraction Diagram

The relative intensities of the main lines are given in the following table.

| Interplanar spacing (Å) | |
| --- | --- |
| 15.5 | 32 |
| 9.9 | 100 |
| 5.3 | 59 |
| 4.7 | 47 |
| 3.5 | 36 |

EXAMPLE 16

Working as described above in Example 1, but using 97 mg of pristinamycin IIB and 80 mg of 4-ζ-ethoxyde(4-ζ-dimethylamino)pristinamycin $I_A$ in 0.7 cm³ of acetone, 100 mg of the co-crystallized combination of 2 molecules of pristinamycin $I_A$ and one molecule of 4-ζ-ethoxyde(4-ζ-dimethylamino)pristinamycin IIB are obtained in the form of white crystals melting at 196° C., giving a titre of 54.6% pristinamycin IIB and 45.4% 4-ζ-ethoxyde(4-ζ-dimethylamino)pristinamycin $I_A$.

EXAMPLE 17

Working as described above in Example 1, but using 56 mg of pristinamycin IIB and 47 mg of 4-70-allyloxyde(4-ζ-dimethylamino)pristinamycin $I_A$ in 0.5 cm³ of acetone, 67 mg of the co-crystallized combination of 2 molecules of pristinamycin $I_A$ and one molecule of 4-ζ-allyloxyde(4-ζ-dimethylamino)pristinamycin IIB are obtained in the form of white crystals melting at 196° C., giving a titre of 57.1% pristinamycin IIB and 42.9% 4-ζ-allyloxyde(4-ζ-dimethylamino)pristinamycin $I_A$.

EXAMPLE 18

Working as described above in Example 1, but using 62 mg of pristinamycin IIB and 53 mg of 4-ζ-ethylaminode(4-ζ-dimethylamino)pristinamycin $I_A$ in 0.6 cm³ of acetone, 47 mg of the co-crystallized combination of 2 molecules of pristinamycin $I_A$ and one molecule of 4-ζ-ethylaminode(4-ζ-dimethylamino)pristinamycin IIB are obtained in the form of white crystals melting at 188° C., giving a titre of 55.7% pristinamycin IIB and 44.3% 4-ζ-ethylaminode(4-ζ-dimethylamino)pristinamycin $I_A$.

EXAMPLE 19

Working as described above in Example 1, but using 178 mg of pristinamycin IIB and 153 mg of 4-ζ-trifluoromethoxyde(4-ζ-dimethylamino)pristinamycin $I_A$ in 1.8 cm³ of acetone, 188 mg of the co-crystallized combination of 2 molecules of pristinamycin $I_A$ and one molecule of 4-ζ-trifluoromethoxyde(4-ζ-dimethylamino) pristinamycin IIB are obtained in the form of white crystals melting at 184° C., giving a titre of 54.1% pristinamycin IIB and 45.9% 4-ζ-trifluoromethoxyde(4-ζ-dimethylamino) pristinamycin $I_A$.

X-ray Diffraction Diagram

The relative intensities of the main lines are given in the following table.

| Interplanar spacing (Å) | |
| --- | --- |
| 15.7 | 71 |
| 5.9 | 52.4 |
| 5.2 | 100 |
| 5 | 73 |
| 4.7 | 41.1 |

EXAMPLE 20

Working as described above in Example 1, but using 61 mg of pristinamycin IIB and 50 mg of 4-ε-methylthiode(4-ζ-dimethylamino)pristinamycin $I_A$ in 0.6 cm³ of acetone, 38 mg of the co-crystallized combination of 2 molecules of pristinamycin $I_A$ and one molecule of 4-ε-methylthiode(4-ζ-dimethylamino)pristinamycin IIB are obtained in the form of white crystals melting at 188° C., giving a titre of 53.1% pristinamycin IIB and 46.9% 4-ε-methylthiode(4-ζ-dimethylamino)pristinamycin $I_A$.

X-ray Diffraction Diagram

The relative intensities of the main lines are given in the following table.

| Interplanar spacing (Å) | |
| --- | --- |
| 15.8 | 100 |
| 10.4 | 38 |
| 5.9 | 53 |
| 5.2 | 61 |
| 5.0 | 51 |

EXAMPLE 21

Working as described above in Example 1, but using 35 mg of pristinamycin IIB and 30 mg of 4-ζ-(allylethylamino) de(4-ζ-dimethylamino)pristinamycin $I_A$ in 0.3 cm³ of acetone, 30 mg of the co-crystallized combination of 2 molecules of pristinamycin $I_A$ and one molecule of 4-ζ-(allylethylamino)de(4-ζ-dimethylamino)pristinamycin IIB are obtained in the form of white crystals melting at 174° C., giving a titre of 52.3% pristinamycin IIB and 47.7% 4-ζ-(allylethylamino)de(4-ζ-dimethylamino)pristinamycin $I_A$.

EXAMPLE 22

Working as described above in Example 1, but using 42 mg of pristinamycin IIB and 36 mg of 4-ζ-(ethylpropylamino)de(4-ζ-dimethylamino)pristinamycin $I_A$ in 0.5 cm³ of acetone, 16 mg of the co-crystallized combination of 2 molecules of pristinamycin $I_A$ and one molecule of 4-ζ-(ethylpropylamino)de(4-ζ-dimethylamino) pristinamycin IIB are obtained in the form of white crystals melting at 193° C., giving a titre of 51% pristinamycin IIB and 49% 4-ζ-(ethylpropylamino)de(4-ζ-dimethylamino) pristinamycin

PREPARATION OF THE COMPONENTS OF THE B GROUP

EXAMPLE A

4-ε-Chloropristinamycin $I_A$ 8 g of pristinamycin $I_A$ in 80 cm³ of acetonitrile are placed in a round-bottomed flask and 1.39 g of N-chlorosuccinimide are then added. The mixture is heated at reflux for 16 hours 30 minutes, then 0.12 g of N-chlorosuccinimide is added and the refluxing is continued for 3 hours. The reaction mixture is concentrated to dryness under reduced pressure (2.7 kPa) at 30° C. The solid obtained is taken up in 50 cm³ of dichloromethane and 60 cm³ of distilled water to which sodium chloride is added, the aqueous phase is separated out after settling has taken place and the organic phase is then washed with 50 cm³ of distilled water saturated with sodium chloride. The organic phase is separated out after settling has taken place, dried over magnesium sulphate, filtered and then concentrated to dryness under reduced pressure (2.7 kPa) at 30° C. to give a yellow solid which is recrystallized from 100 cm³ of refluxing 1-propanol and then a second time from 50 cm³ of refluxing 1-propanol. After cooling, filtering off the crystals and drying under reduced pressure (135 Pa) at 50° C., 3 g of 4-ε-chloropristinamycin $I_A$ are obtained in the form of light-beige crystals melting at 220° C.

Proton NMR spectrum (300 MHz, CDCl₃, δ in ppm): 0.58 (dd, J=16 and 6 Hz, 1H, 5 $β_2$), 0.91 (t, J=7.5 Hz, 3H: $CH_3$ 2 γ), from 1.05 to 1.35 (mt, 2H: 3 $β_2$ and 3 $γ_2$), 1.32 (d, J=7.5 Hz, 3H: $CH_3$ 1 γ), from 1.50 to 1.85 (mt, 3H: 3 $γ_1$ and $CH_2$ 2 β), 2.03 (mt, 1H: 3 $β_1$), 2.17 (mt, 1H: 5 $δ_2$), 2.39 (broad d, J=16 Hz, 1H: 5 $δ_1$), 2.44 (d, J=16 Hz, 1H: 5 $β_1$), 2.77 (s, 6H: $N(CH_3)_2$ 4), 2.85 (dt, J=13.5 and 4.5 Hz, 1H: 5 $ε_2$), 2.97

(dd, J=12 and 5 Hz, 1H: 4 $\beta_2$), 3.23 (s, 3H: NCH$_3$ 4), 3.35 (t, J=12 Hz, 1H: 4 $\beta_1$), 3.30 and 3.58 (2 mts, 1H each: CH$_2$ 3 $\delta$), 4.57 (dd, J=8 and 7.5 Hz, 1H: 3 $\alpha$), 4.76 (broad dd, J=13.5 and 8 Hz, 1H: 5 $\epsilon_1$), 4.85 (mt, 1H: 2$\alpha$), 4.90 (dd, J=10 and 1.5 Hz, 1H: 1$\alpha$), 5.25 (dd, J=12 and 5 Hz, 1H: 4 $\alpha$), 5.31 (broad d, J=6 Hz, 1H: 5 $\alpha$), 5.86 (d, J=9.5 Hz, 1H: 6 $\alpha$), 5.90 (mt, 1H: 1$\beta$), 6.50 (d, J=10 Hz, 1H: NH 2), 6.97 (d, J=8 Hz, 1H: H 5 of the aromatic at 4), 7.08 (dd, J=8 and 2 Hz, 1H: H 6 of the aromatic at 4), from 7.15 to 7.40 (mt, 6H: aromatic H at 6 and H 2 of the aromatic at 4), 7.43 (dd, J=8.5 and 2 Hz, 1H: 1' H$_4$), 7.52 (dd, J=8.5 and 4.5 Hz, 1H: 1' H$_5$), 7.83 (dd, J=4.5 and 2 Hz, 1H: 1' H$_6$), 8.38 (d, J=10 Hz, 1H: NH 1), 8.73 (d, J=9.5 Hz, 1H: NH 6), 11.65 (s, 1H: OH).

EXAMPLE B

4-$\epsilon$-Bromopristinamycin I$_A$ 30 g of pristinamycin I$_A$ in 300 cm$^3$ of dichloromethane are placed in a round-bottomed flask and 6.85 g of N-bromosuccinimide are then added. The mixture is stirred at room temperature for 29 hours and is then concentrated to dryness under reduced pressure. The solid obtained is stirred in 400 cm$^3$ of diethyl ether, filtered off and then washed with twice 100 cm$^3$ of diethyl ether. After filtration, the solid is triturated for 45 minutes in 400 cm$^3$ of distilled water, filtered off and then washed with twice 150 cm$^3$ of water. The solid obtained is dried and then recrystallized from 1600 cm$^3$ of refluxing ethanol. After cooling, filtering off the crystals and drying under reduced pressure (135 Pa) at 50° C., 23.2 g of 4-$\epsilon$-bromopristinamycin I$_A$ are obtained in the form of white crystals melting at 220° C.

Proton NMR spectrum (300 MHz, CDCl$_3$, $\delta$ in ppm): 0.58 (dd, J=16 and 6 Hz, 1H, 5 $\beta_2$), 0.91 (t, J=7.5 Hz, 3H: CH$_3$ 2 $\gamma$), from 1.10 to 1.40 (mt, 2H: 3 $\beta_2$ and 3 $\gamma_2$) 1.32 (d, J=7.5 Hz, 3H: CH$_3$ 1 $\gamma$), from 1.50 to 1.85 (mt, 3H: 3 $\gamma_1$ and CH$_2$ 2 $\beta$), 2.03 (mt, 1H: 3 $\beta_1$), 2.19 (mt, 1H: 5 $\delta_2$), 2.39 (broad d, J=16 Hz, 1H: 5 $\delta_1$), 2.44 (d, J=16 Hz, 1H: 5 b$_1$), 2.76 (s, 6H: N(CH$_3$)$_2$ 4), 2.83 (dt, J=13.5 and 4 Hz, 1H: 5 $\epsilon_2$), 2.97 (dd, J=12.5 and 4.5 Hz, 1H: 4 $\beta_2$), 3.23 (s, 3H: NCH$_3$ 4), 3.30 and 3.57 (2 mts, 1H each: CH$_2$ 3 $\delta$), 3.33 (t, J=12.5 Hz, 1H: 4 $\beta_1$), 4.55 (dd, J=8 and 7.5 Hz, 1H: 3 $\alpha$), 4.74 (broad dd, J=13.5 and 8 Hz, 1H: 5 $\epsilon_1$), 4.84 (mt, 1H: 2$\alpha$), 4.92 (dd, J=10 and 2 Hz, 1H: 1$\alpha$), 5.27 (dd, J=12.5 and 4.5 Hz, 1H: 4 $\alpha$), 5.33 (broad d, J=6 Hz, 1H: 5 $\alpha$), 5.88 (d, J=9.5 Hz, 1H: 6 $\alpha$), 5.90 (mt, 1H: 1$\beta$), 6.53 (d, J=10 Hz, 1H: NH 2), 7.00 (d, J=8 Hz, 1H: H 5 of the aromatic at 4), 7.12 (dd, J=8 and 2 Hz, 1H: H 6 of the aromatic at 4), from 7.15 to 7.40 (mt, 5H: aromatic H at 6), 7.43 (dd, J=8.5 and 2 Hz, 1H: 1' H$_4$), 7.46 (d, J=2 Hz, 1H: H 2 of the aromatic at 4), 7.52 (dd, J=8.5 and 4.5 Hz, 1H: 1' H$_5$), 7.87 (dd, J=4.5 and 2 Hz, 1H: 1' H$_6$), 8.41 (d, J=10 Hz, 1H: NH 1), 8.74 (d, J=9.5 Hz, 1H: NH 6), 11.65 (s, 1H: OH).

EXAMPLE C

4-$\epsilon$-Chloropristinamycin I$_B$

Working as in Example A, but starting with 1.7 g of pristinamycin I$_B$ and 320 mg of N-chlorosuccinimide in 17 cm$^3$ of acetonitrile, and after refluxing the reaction mixture for 1 hour 30 minutes and then concentrating to dryness, 1.8 g of a beige-coloured solid are obtained, which product is purified by flash chromatography (98/2 dichloro-methane/ methanol eluent) to give 1.2 g of 4-$\epsilon$-chloropristinamycin I$_B$ in the form of a pale yellow solid melting at 198° C.

Proton NMR spectrum (400 MHz, CDCl$_3$, $\delta$ in ppm): 0.79 (dd, J=16 and 5.5 Hz, 1H: 5 $\beta_2$), 0.91 (t, J=7.5 Hz, 3H: CH$_3$ 2 $\gamma$), 1.15 (mt, 1H: 3 $\beta_2$), from 1.25 to 1.40 (mt, 3H: 3 $\gamma_2$), 1.34 (d, J=7.5 Hz, 3H: CH$_3$ 1, $\gamma$), from 1.50 to 1.85 (mt, 3H: 3 $\gamma_1$ and CH$_2$ 2 $\beta$), 2.03 (mt, 1H: 3 $\beta_1$), 2.23 (mt, 1H: 5 $\delta_2$), 2.40 (broad d, J=16 Hz, 1H: 5 $\delta_1$), 2.47 (d, J=16 Hz, 1H: 5 $\beta_1$), 2.85 (dt, J=13 and 4 Hz, 1H: 5 $\epsilon_2$), from 2.85 to 2.90 (mt, 1H: 4 $\beta_2$), 2.88 (s, 3H: ArNCH$_3$ 4), 3.25 (s, 3H: NCH$_3$ 4), 3.28 and 3.58 (2 mts, 1H each: CH$_2$ 3 $\delta$), 3.31 (t, J=12 Hz, 1H: 4 $\beta_1$), 4.40 (unres. mult., 1H: ArNH), 4.57 (t, J=7.5 Hz, 1H: 3 $\alpha$), 4.78 (broad dd, J=13 and 8 Hz, 1H: 5 $\epsilon_1$), 4.84 (mt, 1H: 2$\alpha$), 4.91 (broad d, J=10 Hz, 1H: 1$\alpha$), 5.23 (dd, J=12 and 5 Hz, 1H: 4 $\alpha$), 5.36 (broad d, J=5.5 Hz, 1H: 5 $\alpha$), 5.89 (d, J=9.5 Hz, 1H: 6 $\alpha$), 5.90 (mt, 1H: 1$\beta$), 6.51 (d, J=10 Hz, 1H: NH 2), 6.55 (d, J=8 Hz, 1H: H 5 of the aromatic at 4), 7.02 (dd, J=8 and 2 Hz, 1H: H 6 of the aromatic at 4), 7.13 (d, J=2 Hz, 1H: H 2 of the aromatic at 4), from 7.15 to 7.40 (mt, 5H: aromatic H at 6), 7.43 (broad d, J=8.5 Hz, 1H: 1' H$_4$), 7.52 (dd, J=8.5 and 4.5 Hz, 1H: 1' H$_5$), 7.79 (broad d, J=4.5 Hz, 1H: 1' H$_6$), 8.40 (d, J=10 Hz, 1H: NH 1), 8.75 (d, J=9.5 Hz, 1H: NH 6), 11.63 (s, 1H: OH).

EXAMPLE D

4-$\epsilon$-Bromopristinamycin I$_B$

Working as in Example B, but starting with 2 g of pristinamycin I$_B$ and 420 mg of N-bromosuccinimide in 30 cm$^3$ of dichloromethane, and after stirring the mixture at room temperature for 1 hour 30 minutes and then concentrating to dryness, 2.1 g of a beige-coloured solid are obtained, which product is purified by flash chromatography (98/2 dichloro-methane/methanol eluent) to give 1.7 g of 4-$\epsilon$-bromopristinamycin I$_B$ in the form of a white solid melting at 220° C.

Proton NMR spectrum (400 MHz, CDCl$_3$, $\delta$ in ppm): 0.80 (dd, J=16 and 5.5 Hz, 1H: 5 $\beta_2$), 0.90 (t, J=7.5 Hz, 3H: CH$_3$ 2 $\gamma$), 1.13 (mt, 1H: 3 $\beta_2$), from 1.20 to 1.40 (mt, 1H: 3 $\gamma_2$), 1.33 (d, J=7.5 Hz, 3H: CH$_3$ 1 $\gamma$), from 1.50 to 1.85 (mt, 3H: 3 $\gamma_1$ and CH$_2$ 2 $\beta$), 2.03 (mt, 1H: 3 $\beta_1$), 2.28 (mt, 1H, 5 $\delta_2$), 2.40 (broad d, J=16 Hz, 1H: 5 $\delta_1$), 2.46 (d, J=16 Hz, 1H: 5 $\beta_1$), 2.85 (dt, J=13 and 5 Hz, 1H: 5 $\epsilon_2$), 2.88 (d, J=5.5 Hz, 3H: ArNCH$_3$ 4), 2.90 (dd, J=12 and 4 Hz, 1H: 4 $\beta_2$), 3.24 (s, 3H: NCH$_3$ 4), 3.30 and 3.58 (2 mts, 1H each: CH$_2$ 3 $\delta$), 3.31 (t, J=12 Hz, 1H: 4 $\beta_1$), 4.41 (q, J=5.5 Hz, 1H: ArNH), 4.57 (t, J=7.5 Hz, 1H: 3 $\alpha$), 4.78 (broad dd, J=13 and 8 Hz, 1H: 5 $\epsilon_1$), 4.85 (mt, 1H: 2$\alpha$), 4.91 (broad d, J=10 Hz, 1H: 1$\alpha$), 5.24 (dd, J=12 and 4 Hz, 1H: 4 $\alpha$), 5.37 (broad d, J=5.5 Hz, 1H: 5 $\alpha$), 5.89 (d, J=9.5 Hz, 1H: 6 $\alpha$), 5.90 (mt, 1H: 1$\beta$), 6.51 (d, J=10 Hz, 1H: NH 2), 6.53 (d, J=8 Hz, 1H: H 5 of the aromatic at 4), 7.05 (dd, J=8 and 2 Hz, 1H: H 6 of the aromatic at 4), from 7.15 to 7.40 (mt, 6H: aromatic H at 6 and H 2 of the aromatic at 4), 7.43 (broad d, J=8.5 Hz, 1H: 1' H$_4$), 7.48 (dd, J=8.5 and 5 Hz, 1H: 1' H$_5$), 7.79 (broad d, J=5 Hz, 1H: 1' H$_6$), 8.40 (d, J=10 Hz, 1H: NH 1), 8.76 (d, J=9.5 Hz, 1H: NH 6), 11.63 (s, 1H: OH).

EXAMPLE E

4-$\epsilon$-Allylpristinamycin IA 7.07 g of sodium acetate in 100 cm$^3$ of distilled water are placed in a three-necked flask maintained under a nitrogen atmosphere. The solution is brought to reflux and a solution of 15.5 g of 4-N-allylammoniopristinamycin I$_A$ bromide in 100 cm$^3$ of distilled water is then added via a dropping funnel. After reacting for 2 hours, 1 g of sodium acetate is added and the mixture is stirred at reflux for 22 hours. A further portion of 5 g of sodium acetate is added and the reaction is continued for 20 hours. The precipitate formed is filtered off while hot, rinsed with twice 50 cm$^3$ of distilled water and then dried under reduced pressure (2.75 kPa) to give 7 g of a white solid which is purified by flash chromatography (eluent: 70/30 toluene/acetone) to give 4.6 g of 4-$\epsilon$-allylpristinamycin I$_A$ in the form of a white solid melting at 160° C.

Proton NMR spectrum (400 MHz, CDCl$_3$, $\delta$ in ppm): 0.42 (dd, J=16 and 5.5 Hz, 1H: 5 $\beta_2$), 0.92 (t, J=7.5 Hz, 3H: CH$_3$ 2 γ), from 1.15 to 1.40 (mt, 2H: 3 β$_2$ and 3 γ$_2$), 1.33 (d, J=7.5 Hz, 3H: CH$_3$ 1 γ), from 1.55 to 1.80 (mt, 3H: 3 γ$_1$ and CH$_2$ 2 β), from 2.00 to 2.15 (mt, 2H: 3 β$_1$ and 5 δ$_2$), 2.30 (broad d, J=16 Hz, 1H: 5 δ$_1$), 2.33 (d, J=16 Hz, 1H: 5 β$_1$), 2.63 (s, 6H: N(CH$_3$)$_2$ 4), 2.76 (dt, J=13.5 and 4.5 Hz, 1H: 5 ε$_2$), 2.98 (dd, J=12 and 4.5 Hz, 1H: 4 β$_2$), from 3.20 to 3.40 (mt, 3H: 4 β$_1$- 3 δ$_1$ and 1H of the allylic ArCH$_2$), 3.25 (s, 3H: NCH$_3$ 4), 3.48 (dd, J=16 and 6.5 Hz, 1H: other H of the allylic ArCH$_2$), 3.56 (mt, 1H: 3 δ$_2$), 4.57 (dd, J=6.5 and 7.5 Hz, 1H: 3 α), 4.68 (broad dd, J=13.5 and 7.5 Hz, 1H: 5 ε$_1$), 4.84 (mt, 1H: 2α), 4.90 (broad d, J=10 Hz, 1H: 1α), from 5.00 to 5.15 (mt, 2H: =CH$_2$), 5.23 (broad d, J=5.5 Hz, 1H: 5α), 5.28 (dd, J=12 and 4.5 Hz, 1H: 4α), from 5.80 to 5.95 (mt, 3H: 6 α-1β and allylic CH), 6.53 (d, J=10 Hz, 1H: NH 2) 7.04 (mt, 3H: aromatic H at 4), from 7.15 to 7.40 (mt, 5H: aromatic H at 6), 7.45 (dd, J=8.5 and 2 Hz, 1H: 1' H$_4$), 7.48 (dd, J=8.5 and 4 Hz, 1H: 1' H$_5$), 7.88 (dd, J=4 and 2 Hz, 1H: 1' H$_6$), 8.45 (d, J=10 Hz, 1H: NH 1), 8.76 (d, J=9.5 Hz, 1H: NH 6), 11.64 (s, 1H: OH).

The 4-N-allylammoniopristinamycin I$_A$ bromide may be prepared in the following way: 10 g of pristinamycin I$_A$ dissolved in 25 cm$^3$ of 1,2-dichloroethane are placed in a 3-necked flask maintained under a nitrogen atmosphere, followed by 2.5 cm$^3$ of allyl bromide. The mixture is heated for 7 hours at 40° C. and is then stirred at room temperature for 14 hours. 200 cm$^3$ of toluene are then added with stirring over 10 minutes and the mixture is stirred for 30 minutes. The precipitate formed is filtered off, rinsed with 50 cm$^3$ of toluene and then dried under reduced pressure (135 Pa) at 45° C. to give 10.5 g of a solid which is triturated in 200 cm$^3$ of ethyl acetate at 40° C. and then at room temperature for 1 hour. The solid is filtered off and then dried at 45° C. under reduced pressure (135 Pa) to give 10 g of 4-N-allyl-ammoniopristinamycin I$_A$ bromide in the form of a white solid melting at about 210° C.

Proton NMR spectrum (400 MHz, CDCl$_3$ with addition of a few drops of CD$_3$OD-d4, δ in ppm): 0.75 (t, J=7.5 Hz, 3H: CH$_3$ 2 γ), from 1.00 to 1.35 (mt, 3H: 3 β$_2$-3 γ$_2$ and 5 β$_2$), 1.18 (d, J=7.5 Hz, 3H: CH$_3$ 1 γ), from 1.45 to 1.65 (mt, 3H: 3 γ$_1$ and CH$_2$ 2 β), 1.95 (mt, 1H: 3 β$_1$), 2.15 (mt, 1H: 5 δ$_2$), 2.28 (broad d, J=16 Hz, 1H: 5 δ$_1$), 2.55 (d, J=16 Hz, 1H: 5 β$_1$), 2.72 (dt, J=13.5 and 4.5 Hz, 1H: 5 ε$_2$), 2.95 (s, 3H: NCH$_3$ 4), from 3.10 to 3.50 (mt, 4H: CH$_2$ 4 β and CH$_2$ 3 δ), 3.40 and 3.48 (2s, 6H in total: N(CH$_3$)$_2$ 4), 4.35 (t, J=7.5 Hz, 1H: 3 α), from 4.40 to 4.60 (mt, 3H: allylic NCH$_2$ and 5 ε$_1$), 4.64 (mt, 1H: 2α), 4.93 (broad s, 1H: 1α), from 5.30 to 5.75 (mt, 7H: allylic CH$_2$-5 α-4 α-6 α-1β and allylic CH), 6.88 (d, J=10 Hz, 1H: NH 2), from 7.05 to 7.25 (mt, 8H: aromatic H at 6-1' H$_4$ and 4 δ), 7.35 (dd, J=8 and 4 Hz, 1H: 1' H$_5$), 7.60 (d, J=8.5 Hz), 2H: 4 ε), 7.65 (mt, 1H: 1' H$_6$), 8.58 (d, J=9.5 Hz, 1H: NH 6).

EXAMPLE F
Preparation of 4-ζ-tert-butylde(4-ζ-dimethylamino)pristinamycin I$_A$ A culture of the strain SP92::pVRC508 in production medium is produced on a 60-conical-flask scale with addition at 16 hours of 1 ml of a solution containing 5 g/l of (R,S)-4-tert-butylphenylalanine in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile, and then centrifuged. The supernatant is extracted with twice 0.5 volume of dichloromethane. The chloromethylenic phases are washed with water and then combined, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin I$_A$ derivative are pooled and evaporated. The dry residue is taken up in 7 ml of a 60% water and 40% acetonitrile mixture and injected in two portions onto a Nucleosil 7μ C8 10×250 mm semi-preparative column (Macherey Nagel) eluted in a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 30 mg of 4-ζ-tert-butylde(4-ζ-dimethylamino)-pristinamycin I$_A$ are obtained.

$^1$H NMR spectrum (400 MHz, CDCl$_3$, δ in ppm, ref. TMS): 0.21 (dd, J=16 and 5.5 Hz, 1H: 5 β$_2$), 0.91 (t, J=7.5 Hz, 3H: CH$_3$ 2 γ), 1.17 (mt, 1H: 3 β$_2$), from 1.20 to 1.40 (mt, 1H: 3 γ$_2$), 1.33 (s, 9H: CH$_3$ of the tert-butyl), 1.35 (d, J=7.5 Hz, 3H: 1 γ), from 1.50 to 1.85 (mt, 3H: 3 γ$_1$ and CH$_2$ 2 β), 2.04 (mt, 1H: 3 β$_1$), 2.13 (mt, 1H: 5 δ$_2$), 2.30 (mt, 2H: 5 δ$_1$ and 5 β$_1$), 2.80 (dt, J=13 and 4 Hz, 1H: 5 ε$_2$), 3.00 (dd, J=12 and 4 Hz, 1H: 4 β$_2$), 3.29 (s, 3H: NCH$_3$ 4), 3.31 and 3.59 (2 mts, 1H each: CH$_2$ 3 δ), 3.40 (t, J=12 Hz, 1H: 4 β$_1$), 4.57 (t, J=7.5 Hz, 1H: 3 α), 4.74 (broad dd, J=13.5 and 7 Hz, 1H: 5 ε$_1$), 4.85 (mt, 1H: 2α), 4.90 (broad d, J=10 Hz, 1H: 1α), 5.21 (broad d, J=5.5 Hz, 1H: 5 α), 5.25 (dd, J=12 and 4 Hz, 1H: 4 α), 5.87 (d, J=9 Hz, 1H: 6 α), 5.92 (broad q, J=7.5 Hz, 1H: 1β), 6.56 (d, J=9.5 Hz, 1H: NH 2), from 7.10 to 7.30 (mt, 5H: aromatic H at 6), 7.28 (d, J=7.5 Hz, 2H: 4δ), 7.38 (d, J=7.5 Hz, 2H: 4ε), 7.49 (broad d, J=8.5 Hz, 1H: 1' H$_4$), 7.53 (dd, J=8.5 and 4 Hz, 1H: 1' H$_5$), 7.86 (d, J=4 Hz, 1H: 1' H$_6$), 8.45 (d, J=10 Hz, 1H: NH 1), 8.74 (d, J=9 Hz, 1H: NH 6), 11.65 (s, 1H: OH).

The (R,S)-4-tert-butylphenylalanine hydrochloride may be prepared in the following way:

25 g of diethyl 4-(tert-butyl)benzyl-acetamidomalonate and 250 ml of 37% hydrochloric acid are added to a three-necked flask on which is mounted a condenser. The mixture is stirred and heated at reflux until there is no further evolution of gas. After cooling the reaction mixture, the precipitate obtained is filtered off and then recrystallized from acetonitrile to give 25.6 g of (R,S)-4-tert-butylphenylalanine hydrochloride in the form of a white solid melting at 234° C.

The diethyl 4-(tert-butyl)benzylacetamidomalonate can be prepared in the following way:

25 g of 4-tert-butylbenzyl bromide, 50 ml of anhydrous toluene and 3.1 g of sodium hydride as an 80% suspension in oil are added under a nitrogen atmosphere to a three-necked flask on which is mounted a condenser, followed by addition of 21.8 g of diethyl acetamidomalonate. The mixture is heated at 110° C. for 17 hours. After cooling, 15 ml of absolute ethanol, then 15 ml of 50% ethanol and then 50 ml of water are added slowly using a dropping funnel. The organic phase is separated out after settling has taken place and the aqueous phase is washed with 3 times 50 ml of diethyl ether. The organic phases are combined, washed with water and then dried over sodium sulphate. After filtering and concentrating under reduced pressure, the product is crystallized from petroleum ether to give 25 g of diethyl 4-(tert-butyl)benzylacetamidomalonate in the form of a white solid melting at 80° C.

The mutant SP92::pVRC508 was cultured in liquid production medium. The fermentation was carried out as follows: 0.5 ml of a suspension of spores of the abovementioned strain is added under sterile conditions to 40 ml of inoculum medium in a 300 ml baffle-plated conical flask. The inoculum medium consists of 10 g/l of corn steep, 15 g/l of sucrose, 10 g/l of $(NH_4)_2SO_4$, 1 g/l of $K_2HPO_4$, 3 g/l of NaCl, 0.2 g/l of $MgSO_4.7H_2O$ and 1.25 g/l of $CaCO_3$. The pH is adjusted to 6.9 with sodium hydroxide before introducing calcium carbonate. The, conical flasks are stirred for 44 hours at 27° C. on a rotary stirrer at a speed of 325 rpm. 2.5 ml of the above culture at 44-hours-old are added under sterile conditions to 30 ml of production medium in a 300 ml conical flask. The production medium consists of 25 g/l of soya flour, 7.5 g/l of starch, 22.5 g/l of glucose, 3.5 g/l of forage yeast, 0.5 g/l of zinc sulphate and 6 g/l of calcium carbonate. The pH is adjusted to 6.0 with hydrochloric acid before introducing the calcium carbonate. The conical flasks are stirred at 27° C. on a rotary stirrer at a speed of 325 rpm. After 16 hours, 1 ml of a solution of one of the precursors listed in Table 3 (generally 5 or 10 g/l) is added to the culture. Culturing of the latter is stopped 8 or 24 hours later. The broth is immediately volumized and 2 volumes of mobile phase composed of 34% acetonitrile and 66% 0.1M $KH_2PO_4$ solution (adjusted to pH 2.9 with concentrated $H_3PO_4$) are added, which allows extraction of the pristinamycins. After stirring, the whole mixture is centrifuged and the pristimamycins contained in the supernatant are extracted and purified. They are also assayed by HPLC by injecting 150 µl of the centrifugation supernatant onto a Nucleosil 5-C8 4.6×150 mm column eluted with a mixture of 40% acetonitrile and 60% 0.1M phosphate buffer, pH 2.9.

EXAMPLE G

Preparation of 4-ζ-isopropylde(4-ζ-dimethylamino) pristinamycin $I_A$

A culture of the strain SP92::pVRC508 in production medium is produced on a 60-conical-flask scale with addition at 16 hours of 1 ml of a solution containing 10 g/l of 0.1N (R,S)-4-isopropylphenyl-alanine in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then combined, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. 61 mg of dry residue are obtained. This residue is taken up in 9 ml of a 60% water and 40% acetonitrile mixture and is injected in 3 portions onto a Nucleosil 7µ C8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 51 mg of 4-ζ-isopropylde(4-ζ-dimethylamino) pristinamycin $I_A$ are obtained.

$^1$H NMR spectrum (250 MHz, $CDCl_3$, δ in ppm, ref. TMS): 0.31 (dd, J=16 and 5.5 Hz, 1H: 5 $β_2$), 0.91 (t, J=7.5 Hz, 3H: $CH_3$ 2 γ), from 1.00 to 1.45 (mt, 2H: 3 $β_2$ and 3 $γ_2$), 1.25 (d, J=7.5 Hz, 6H: $CH_3$ of the isopropyl), 1.35 (d, J=7.5 Hz, 3H: $CH_3$ 1 γ), from 1.50 to 1.85 (mt, 3H: 3 $γ_1$ and $CH_2$ 2 β), from 1.95 to 2.20 (mt, 2H: 3 $β_1$ and 5 $δ_2$), 2.30 (mt, 2H: 5 $δ_1$ and 5 $β_1$), 2.80 (dt, J=13 and 4 Hz, 1H: 5 $ε_2$), 2.88 (mt, 1H: CH of the isopropyl), 2.98 (dd, J=12 and 4 Hz, 1H: 4 $β_2$), 3.30 (s, 3H: $NCH_3$ 4), 3.32 and 3.55 (2 mts, 1H each: $CH_2$ 3 δ), 3.38 (t, J=12 Hz, 1H: 4 $β_1$), 4.55 (t, J=7.5 Hz, 1H: 3 α), 4.72 (broad dd, J=13 and 7 Hz, 1H: 5 $ε_1$), 4.85 (mt, 1H: 2α), 4.88 (broad d, J=10 Hz, 1H: 1α), 5.21 (broad d, J=5.5 Hz, 1H: 5 α), 5.25 (dd, J=12 and 4 Hz, 1H: 4 α), 5.87 (d, J=9 Hz, 1H: 6 α), 5.90 (broad q, J=7.5 Hz, 1H: 1β), 6.50 (d, J=9.5 Hz, 1H: NH 2), from 7.05 to 7.35 (mt, 9H: aromatic H at 6-4ε and 4δ), 7.50 (mt, 2H: 1' $H_5$ and 1' $H_4$), 7.86 (dd, J=4 and 1.5 Hz, 1H: 1' $H_6$), 8.40 (d, J=10 Hz, 1H: NH 1), 8.72 (d, J=9 Hz, 1H: NH 6), 11.60 (s, 1H: OH).

The (R,S)-4-isopropylphenylalanine may be prepared in the following way:

7 g of red phosphorus and 8 g of 4-(isopropylbenzylidene)-2-methyl-5-oxazolone in 45 ml of acetic anhydride are placed in a three-necked flask and 35 ml of 57% hydriodic acid are then added slowly with stirring, using a dropping funnel. At the end of the addition, the mixture is heated at reflux for 3 hours 30 minutes and then left at room temperature for 3 days. The reaction mixture is filtered, the solid obtained is rinsed with twice 10 ml of acetic acid and the filtrate is then concentrated to dryness under reduced pressure. The residue obtained is taken up in 100 ml of distilled water and concentrated to dryness under reduced pressure to give a solid which is taken up in 50 ml of distilled water and then extracted with 3 times 50 ml of diethyl ether after addition of 0.5 g of sodium sulphite. The ether is separated out after settling has taken place and the aqueous phase is placed under reduced pressure to remove the traces of diethyl ether. 2 g of animal charcoal are added to the aqueous phase, which is heated to 40–50° C., filtered through Clarcel and then rinsed with a minimum amount of water. The pH is adjusted to 5 by addition, at 4° C., of 32% aqueous ammonia. The precipitate obtained is filtered while cold, rinsed with twice 10 ml of water, 10 ml of ethanol and then with twice 10 ml of ether to give, after drying under reduced pressure at 20° C., 3.97 g of (R,S)-4-isopropylphenylalanine in the form of a white solid melting at a temperature above 260° C.

The 4-(isopropylbenzylidene)-2-methyl-5-oxazolone may be prepared in the following way:

18.52 g of N-acetylglycine, 10.6 g of sodium acetate, 20 ml of 4-isopropylbenzaldehyde and 57 ml of acetic anhydride are placed in a round-bottomed flask fitted with a condenser. The mixture is stirred for 30 minutes and is then stirred at 110° C. for 1 hour, then at room temperature for 15 hours. The reaction mixture is poured into 600 ml of water and 400 ml of petroleum ether preheated to 50° C. The organic phase is separated out after settling has taken place and the aqueous phase is washed with twice 150 ml of petroleum ether.

The organic phases are combined, dried over magnesium sulphate, filtered and concentrated under reduced pressure to 100 ml until a precipitate is obtained. This precipitate is filtered off and washed with twice 50 ml of pentane to give 8.2 g of 4-(isopropylbenzylidene)-2-methyl-5-oxazolone in the form of a yellow solid melting at 77° C.

EXAMPLE H

Preparation of 4-ζ-methoxyde(4-ζ-dimethylamino) pristinamycin $I_A$

A culture of the strain SP92::pVRC508 in production medium is produced on a 12-conical-flask scale with addition at 16 hours of 1 ml of a solution containing 5 g/l of (R,S)-4-methoxyphenylalanine in 0.1N sodium hydroxide. After culturing for 40 hours, the 0.35 liter of broth obtained from the 12 flasks is extracted with 2 volumes of a mixture of 66% 100 mM phosphate buffer pH 2.9 and 34% acetonitrile and is then centrifuged. The supernatant is extracted with, twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. 14 mg of dry residue are obtained. The latter is taken up in 3 ml of a 60% water and 40% acetonitrile mixture and is injected onto a Nucleosil 7μ C8 10×250 mm semi-preparative column (Macherey Nagel) eluted with a mixture of 60% 100 mM phosphate buffer pH 2.9 and 40% acetonitrile. The fractions containing the novel pristinamycin are pooled and extracted with one volume of dichloromethane. The organic phase is washed with water, dried over sodium sulphate and then evaporated. 12 mg of 4-ζ-methoxyde(4-ζ-dimethylamino)pristinamycin $I_A$ are obtained.

$^1$H NMR spectrum (400 MHz, CDCl$_3$, d in ppm, ref. TMS): 0.63 (dd, J=16 and 5.5 Hz, 1H: 5 β$_2$), 0.96 (t, J=7.5 Hz, 3H: CH$_3$ 2 γ), 1.17 (mt, 1H: 3 β$_2$), from 1.30 to 1.45 (mt, 1H: 3 γ$_2$), 1.38 (d, J=7.5 Hz, 3H: CH$_3$ 1 γ), from 1.55 to 1.85 (mt, 3H: 3 γ$_1$ and CH$_2$ 2 β), 2.05 (mt, 1H: 3 β$_1$), 2.20 (mt, 1H: 5 δ$_2$), 2.40 (broad d, J=16 Hz, 1H: 5 δ$_1$), 2.47 (d, J=16 Hz, 1H: 5 β$_1$), 2.88 (dt, J=13 and 4 Hz, 1H: 5 ε$_2$), 2.99 (dd, J=12.5 and 5 Hz, 1H: 4 β$_2$), 3.30 (s, 3H: NCH$_3$ 4), 3.32 and 3.60 (2 mts, 1H each: CH$_2$ 3 δ), 3.40 (t, J=12.5 Hz, 1H: 4 β$_1$), 3.80 (s, 3H: OCH$_3$), 4.60 (t, J=7.5 Hz, 1H: 3 α), 4.80 (broad dd, J=13 and 8.5 Hz, 1H: 5 ε$_1$), 4.88 (mt, 1H: 2α), 4.92 (broad d, J=10 Hz, 1H: 1α), 5.31 (dd, J=12.5 and 5 Hz, 1H: 4 α), 5.34 (broad d, J=5.5 Hz, 1H: 5 α), 5.90 (d, J=9 Hz, 1H: 6 α), 5.93 (broad q, J=7.5 Hz, 1H: 1β), 6.54 (d, J=9 Hz, 1H: NH 2), 6.87 (d, J=8 Hz, 1H: 4ε), 7.16 (d, J=8 Hz, 2H: 4δ), from 7.15 to 7.40 (mt, 5H: aromatic H at 6), 7.50 (mt, 2H: 1' H$_5$ and 1' H$_4$), 7.80 (dd, J=4 and 2.5 Hz, 1H: 1' H$_6$), 8.43 (d, J=10 Hz, 1H: NH 1), 8.78 (d, J=9 Hz, 1H: NH 6), 11.65 (s, 1H: OH).

EXAMPLE I

Preparation of 4-ζ-methylde(4-ζ-dimethylamino) pristinamycin $I_A$

A culture of the strain SP92::pVRC508 in production medium is produced on a 60-conical-flask scale with addition at 16 hours of 1 ml of a solution containing 5 g/l of (R,S)-4-methylphenylalanine in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. 49 mg of dry residue are obtained. The latter is taken up in 6 ml of a 60% water and 40% acetonitrile mixture and is injected in 2 portions onto a Nucleosil 7μ C8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 44 mg of 4-ζ-methylde(4-ζ-dimethylamino)pristinamycin $I_A$ are obtained.

$^1$H NMR spectrum (400 MHz, CDCl$_3$, δ in ppm, ref. TMS): 0.52 (dd, J=16 and 6 Hz, 1H: 5 β$_2$), 0.93 (t, J=7.5 Hz, 3H: CH$_3$ 2 65), 1.15 (mt, 1H: 3 β$_2$), from 1.20 to 1.40 (mt, 1H: 3 γ$_2$), 1.35 (d, J=7.5 Hz, 3H: CH$_3$ 1 γ), from 1.50 to 1.85 (mt, 3H: 3 γ$_1$ and CH$_2$ 2 β), 2.04 (mt, 1H: 3 β$_1$), 2.18 (mt, 1H: 5 67 $_2$), from 2.25 to 2.45 (mt, 2H: 5 δ$_1$ and 5 β$_1$) 2.36 (s, 3H: ArCH$_3$), 2.83 (dt, J=13 and 4 Hz, 1H: 5 ε$_2$), 2.99 (dd, J=13 and 4 Hz, 1H: 4 β$_2$), 3.28 (s, 3H: NCH$_3$ 4), 3.31 and 3.59 (2 mts, 1H each: CH$_2$ 3 δ), 3.40 (t, J=13 Hz, 1H: 4 β$_1$) 4.59 (t, J=7.5 Hz, 1H: 3 α), 4.74 (broad dd, J=13 and 7 Hz, 1H: 5 ε$_1$), 4.85 (mt, 1H: 2α), 4.89 (broad d, J=10 Hz, 1H: 1α), from 5.25 to 5.35 (mt, 2H: 5 α and 4 α), from 5.85 to 5.95 (mt, 2H: 6 α and 1β), 6.52 (d, J=9.5 Hz, 1H: NH 2), 7.14 (limiting AB, J=9 Hz, 4H: 4δ and 4ε), from 7.15 to 7.35 (mt, 5H: aromatic H at 6), 7.50 (mt, 2H: 1' H$_4$ and 1' H$_5$), 7.81 (dd, J=4 and 2 Hz, 1H: 1' H$_6$), 8.41 (d, J=10 Hz, 1H: NH 1), 8.74 (d, J=9 Hz, 1H: NH 6), 11.63 (s, 1H: OH).

EXAMPLE J

Preparation of 4-ζ-methylthiode(4-ζ-dimethylamino) pristinamycin $I_A$

A culture of the strain SP92::pVRC508 in production medium is produced on a 60-conical-flask scale with addition at 16 hours of 1 ml of a solution containing 10 g/l of (R,S)-3-methylaminophenylalanine in water. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. 19 mg of dry residue are obtained. The latter is taken up in 3 ml of a 60% water and 40% acetonitrile mixture and is infected in 2 portions onto a Nucleosil 7μ C8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 45 mg of 4-ζ-methylthiode(4-ζ-dimethylamino) pristinamycin $I_A$ are obtained.

$^1$H NMR spectrum (400 MHz, CDCl$_3$, δ in ppm, ref. TMS): 0.68 (dd, J=16 and 5.5 Hz, 1H: 5 β$_2$), 0.93 (t, J=7.5 Hz, 3H: CH$_3$ 2 γ), 1.13 (mt, 1H: 3 β$_2$), from 1.25 to 1.40 (mt, 1H: 3 γ$_2$), 1.33 (d, J=7.5 Hz, 3H: CH$_3$ 1γ), from 1.55 to 1.85 (mt, 3H: 3 γ$_1$ and CH$_2$ 2 β), 2.02 (mt, 1H: 3 β$_1$), 2.18 (mt, 1H: 5 δ$_2$), 2.38 (broad d, J=16.5 Hz, 1H: 5 δ$_1$), 2.46 (s, 3H: SCH$_3$), 2.48 (d, J=16 Hz, 1H, 5 β$_1$), 2.85 (dt, J=13.5 and 4 Hz, 1H: 5 ε$_2$), 3.00 (dd, J=12 and 5 Hz, 1H: 4 β$_2$) 3.23 (s, 3H: NCH$_3$ 4), 3.37 (t, J=12 Hz, 1H: 4 β$_1$), 3.37 and 3.58 (2 mts, 1H each: CH$_2$ 3 δ), 4.55 (t, J=7.5 Hz, 1H, 3 α), 4.77 (broad dd, J=13.5 and 8 Hz, 1H: 5 ε$_1$), 4.86 (mt 1H: 2α), 4.89 (dd, J=10 and 1.5 Hz, 1H: 1α), 5.30 (broad d, J=5.5 Hz, 1H: 5 α), 5.32 (dd, J=12 and 5 Hz, 1H: 4 α), 5.90 (d, J=9.5 Hz, 1H: 6 α), 5.92 (dq, J=7.5 and 1.5 Hz, 1H: 1β), 6.55 (d, J=9.5 Hz, 1H: NH 2), 7.13 (d, J=8 Hz, 2H: 4δ), from 7.15 to 7.35 (mt, 5H: aromatic H at 6), 7.19 (d, J=8 Hz, 2H: 4ε), 7.45 (mt, 2H: 1' H$_4$ and 1' H$_5$), 7.76 (t, J=5 H, 1H: 1' H$_6$), 8.42 (d, J=10 Hz, 1H: NH 1), 8.76 (d, J=9.5 Hz, 1H: NH 6), 11.65 (s, 1H: OH).

The (R,S)-4-methylthiophenylalanine may be prepared according to the method described by R. L. Colescott, R. R. Herr, J. P. Dailey J. Am. Chem. Soc. 1957, 79, 4232–4235.

EXAMPLE K

Preparation of 4-ε-methylaminode(4-ζ-dimethylamino) pristinamycin I$_A$

A culture of the strain SP92::pVRC508 in production medium is produced on a 60-conical-flask scale with addition at 16 hours of 1 ml of a solution containing 10 g/l of (R,S)-3-methylaminophenylalanine in water. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin I$_A$ derivative are pooled and evaporated. 19 mg of dry residue are obtained. The latter is taken up in 3 ml of a 60% water and 40% acetonitrile mixture and is injected onto a Nucleosil 7μ C8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 8 mg of 4-ε-methylthiode(4-ζ-dimethylamino)pristinamycin I$_A$ are obtained.

$^1$H NMR spectrum (400 MHz, CDCl$_3$, δ in ppm, ref. TMS): 0.93 (t, J=7.5 Hz , 3H: CH$_3$ 2 γ), 1.00 (dd, J=16 and 6 Hz , 1H: 5 β$_2$), 1.17 (mt, 1H: 3 β$_2$), from 1.25 to 1.40 (mt, 2H: 3 γ$_2$), 1.35 (d, J=7.5 Hz , 3H: CH$_3$ 1 γ), from 1.55 to 1.80 (mt, 3H: 3 γ$_1$ and CH$_2$ 2 β), 2.03 (mt, 1H: 3 β$_1$), 2.23 (mt, 1H: 5 δ$_2$), 2.39 (broad d, J=16 Hz , 1H: 5 δ$_1$), 2.52 (d, J=16 Hz , 1H: 5 β$_1$) 2.78 (s, 3H: ArNCH$_3$ 4), 2.85 (dt, J=13 and 4 Hz , 1H: 5 ε$_2$), 2.99 (dd, J=13 and 4.5 Hz , 1H: 4 β$_2$), 3.23 (s, 3H: NCH$_3$ 4), 3.25 (t, J=13 Hz , 1H: 4 β$_1$), 3.38 and 3.58 (2 mts, 1H each: CH$_2$ 3 δ), 4.05 (unres. mult., 1H: ArNH), 4.58 (dd, J=6.5 and 7.5 Hz , 1H: 3 α), 4.76 (broad dd, J=13 and 8 Hz , 1H: 5 ε$_1$), 4.85 (mt, 1H: 2α), 4.87 (broad d, J=10 Hz , 1H: 1α), 5.35 (dd, J=13 and 4.5 Hz , 1H: 4 α), 5.38 (broad d, J=6 Hz , 1H: 5 α), 5.90 (d, J=9.5 Hz , 1H: 6 α), 5.91 (mt, 1H: 1β), 6.36 (broad s, 1H: H 2 of the aromatic at 4), from 6.45 to 6.55 (mt, 2H: H 4 and H 6 of the aromatic at 4), 6.53 (d, J=10 Hz , 1H: NH 2), 7.12 (t, J=8 Hz , 1H: H5 of the aromatic at 4), from 7.15 to 7.45 (mt, 5H: aromatic H at 6), 7.35 (mt, 2H: 1' H$_4$ and 1' H$_5$), 7.75 (t, J=3 Hz , 1H: 1' H$_6$), 8.40 (d, J=10 Hz , 1H: NH 1), 8.78 (d, J=9.5 Hz , 1H: NH 6), 11.60 (s, 1H: OH).

The (R,S)-3-methylaminophenylalanine dihydrochloride may be prepared in the following way:

Working as in Example F, but starting with 1.17 g of diethyl 3-methylaminobenzylacetamidomalonate and 20 ml of 12 N hydrochloric acid, 1.03 g of a beige-yellow solid are obtained. This solid is dissolved in 20 ml of absolute ethanol and 0.4 g of animal charcoal is added. The solution is filtered through Clarcel and then filtered and concentrated under reduced pressure (50 kPa). The same operation is repeated with 1 g of animal charcoal and the solid obtained is triturated in 20 ml of ether. After filtering and drying under reduced pressure (2.7 kPa) at 50° C., 0.65 g of (R,S)-3-methylaminophenylalanine dihydrochloride is obtained in the form of a white powder melting at about 135° C. (decomposition).

The diethyl 3-methylaminobenzylacetamidomalonate may be prepared in the following way:

3.11 ml of acetic anhydride are placed in a three-necked flask maintained under a nitrogen atmosphere. 1.51 ml of formic acid are then added over 3 minutes at 0° C. and the mixture is then heated at 50° C. for 2 hours. The mixture is allowed to cool to room temperature with stirring for 3 hours 20 minutes, 4 ml of anhydrous THF are added under nitrogen and the mixture is cooled to −20° C. A solution of 4 g of diethyl 3-aminobenzylacetamidomalonate in a mixture of 15 ml of anhydrous THF and 15 ml of anhydrous dichloromethane is added over 10 minutes. Stirring is continued for 1 hour 10 minutes at −20° C. and then for 16 hours at 20° C. The reaction mixture is concentrated to dryness under reduced pressure (50 kPa) at 30° C. and then co-evaporated with 30 ml of anhydrous toluene to give a white solid which is dissolved in a mixture of 10 ml of anhydrous THF and 20 ml of anhydrous 1,2-dichloroethane and then placed in a three-necked flask under nitrogen.

The mixture is cooled to −5° C. and 1.55 ml of borane/dimethyl sulphide complex (2M solution in THF) are then added over 10 minutes. The mixture is allowed to warm to room temperature and the solution is heated at reflux for 3 hours and then stirred at room temperature for 15 hours. The reaction mixture is cooled to 0° C. and 10 ml of MeOH are then added over 25 minutes. The mixture is stirred for 45 minutes at 0° C. and then for 30 minutes at room temperature. It is cooled to 0° C. and HCl gas is bubbled in to pH 2. The mixture is heated at reflux for 1 hour and is then concentrated to dryness under reduced pressure at 30° C. to give 5 g of a product which is taken up in 30 ml of aqueous NaHCO$_3$ solution and 30 ml of CH$_2$Cl$_2$. The organic phase is separated out after settling has taken place and the aqueous phase is washed with 20 ml of water. The organic phases are combined, dried over magnesium sulphate, filtered and then concentrated to dryness under reduced pressure (2.6 kPa) to give 3.43 g of a yellow oil, which is purified by flash chromatography (50/50 EtOAc/cyclohexane eluent). After drying under reduced pressure (2.7 kPa) at 20° C., 1.18 g of diethyl 3-methylaminobenzylacetamidomalonate are thus obtained in the form of a light-beige solid melting at 122° C.

The diethyl 3-aminobenzylacetamidomalonate may be prepared as described by T. S. Osdene, D. N. Ward, W. H. Chapman and H. Rakoff, J. Am. Chem. Soc., 81, 1959, 3100–3102.

EXAMPLE L

Preparation of 4-ζ-trifluoromethylde(4-ζ-dimethylamino) pristinamycin I$_A$.

A culture of the strain SP92::pVRC508 in production medium is produced on a 60-conical-flask scale with addition at 16 hours of 1 ml of a solution containing 5 g/l of (S)-4-trifluoromethylphenylalanine in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin I$_A$ derivative are pooled and evaporated. The dry residue is taken up in 3 ml of a 60% water and 40% acetonitrile mixture and is injected onto a Nucleosil 7μC8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 5 mg of 4-ζ-trifluoromethylde(4-ζ-dimethylamino)pristinamycin $I_A$ are obtained.

NMR spectrum $^1$H (400 MHz, CDCl$_3$, δ in ppm, ref. TMS): 0.86 (dd, J=16 and 5.5 Hz , 1H: 5 β$_2$), 0.91 (t, J=7.5 Hz , 3H: CH$_3$ 2 γ), 1.13 (mt, 1H: 3 β$_2$), 1.31 (d, J=7.5 Hz , 3H: CH$_3$ 1 γ), 1.42 (mt, 1H: 3 γ$_2$), from 1.55 to 1.80 (mt, 3H: 3 γ$_1$ and CH$_2$ 2 β), 2.02 (mt, 1H: 3 β$_1$), 2.15 (mt, 1H: 5 δ$_2$), 2.40 (broad d, J=16.5 Hz , 1H: 5 δ$_1$), 2.55 (d, J=16 Hz , 1H: 5 β$_1$), 2.88 (dt, J=14 and 4 Hz , 1H: 5 ε$_2$), 3.18 (s, 3H: NCH$_3$ 4), 3.20 and 3.31 (2 dd, J=13 and 6 Hz and J=13 and 10 Hz respectively, 1H each: 4 β$_2$ and 4 β$_1$), 3.42 and 3.60 (2 mts, 1H each: CH$_2$ 3 δ), 4.50 (t, J=7.5 Hz , 1H: 3 α), 4.73 (broad dd, J=14 and 7.5 Hz , 1H: 5 ε$_1$), 4.83 (mt, 1H: 2α), 4.91. (broad d, J=10 Hz , 1H: 1α), 5.40 (broad d, J=5.5 Hz , 1H: 5 α), 5.55 (dd, J=10 and 6 Hz , 1H: 4 α), 5.87 (d, J=9.5 Hz , 1H: 6 α), 5.90 (broad q, J=7.5 Hz , 1H: 1β), 6.68 (d, J=9.5 Hz , 1H: NH 2), from 7.15 to 7.40 (mt, 9 H: 4δ-aromatic H at 6-1' H$_5$ and 1' H$_4$), 7.52 (d, J=8 Hz , 2H: 4ε), 7.68 (d, J=4 and 1.5 Hz , 1H: 1' H$_6$), 8.43 (d, J=10 Hz , 1H: NH 1), 8.76 (d, J=9.5 Hz , 1H: NH 6), 11.70 (s, 1H: OH).

EXAMPLE M

Preparation of 4-ε-methoxyde(4-ζ-dimethylamino)pristinamycin $I_A$

A culture of the strain SP92::pVRC508 in production medium is produced on a 60-conical-flask scale with addition at 16 hours of 1 ml of a solution containing 5 g/l of (S)-3-methoxyphenylalanine in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. 41 mg of dry residue are obtained. This residue is taken up in 6 ml of a 60% water and 40% acetonitrile mixture and is injected in 2 portions onto a Nucleosil 7μ C8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 28 mg of 4-ε-methoxyde(4-ζ-dimethylamino)pristinamycin $I_A$ are obtained.

$^1$H NMR spectrum (400 MHz, CDCl$_3$, δ in ppm, ref. TMS): 0.52 (dd, J=16 and 5.5 Hz , 1H: 5 β$_2$), 0.90 (t, J=7.5 Hz , 3H: CH$_3$ 2 γ), from 1.10 to 1.34 (mt, 2H: 3 β$_2$ and 3 γ$_2$), 1.34 (d, J=7.5 Hz , 3H: CH$_3$ 1γ), from 1.50 to 1.80 (mt, 3H: 3 γ$_1$ and CH$_2$ 2 β), 2.04 (mt, 1H: 3 β$_1$), 2.20 (Mt, 1H: 5 δ$_2$), 2.35 (broad d, J=16 Hz , 1H: 5 δ$_1$) 2.38 (d, J=16 Hz , 1H: 5 β$_1$), 2.83 (dt, J=13 and 4 Hz , 1H: 5 ε$_2$), 2.97 (dd, J=12 and 4 Hz , 1H: 4 β$_2$), 3.28 (s, 3H: NCH$_3$ 4), 3.28 and 3.56 (2 mts, 1H each: CH$_2$ 3 δ), 3.40 (t, J=12 Hz , 1H: 4 β$_1$), 3.80 (s, 3H: OCH$_3$), 4.58 (t, J=7.5 Hz , 1H: 3 α), 4.76 (broad dd, J=13 and 8 Hz , 1H: 5 ε$_1$), 4.85 (mt, 1H: 2α), 4.90 (broad d, J=10 Hz , 1H: 1α), 5.27 (dd, J=12 and 4 Hz , 1H: 4 α), 5.30 (broad d, J=5.5 Hz , 1H: 5 α), 5.89 (d, J=9.5 Hz , 1H: 6 α), 5.91 (broad q, J=7.5 Hz , 1H: 1β), 6.51 (d, J=10 Hz , 1H: NH 2), from 6.80 to 6.90 (mt, 3H: H 2–H 4 and H 6 of the aromatic at 4), from 7.15 to 7.40 (mt, 6H: H5 of the aromatic at 4 and aromatic H at 6), 7.45 (broad d, J=9 Hz, 1H: 1' H$_4$), 7.50 (dd, J=9 and 4 Hz , 1H: 1' H$_5$), 7.80 (broad d, J=4 Hz , 1H: 1' H$_6$), 8.40 (d, J=10 Hz , 1H: NH 1), 8.73 (d, J=9.5 Hz, 1H: NH 6), 11.62 (s, 1H: OH).

EXAMPLE N

Preparation of 4-ε-fluoro-4-ζmethylde(4-ζdimethylamino) pristinamycin $I_A$

A culture of the strain SP92::pVRC508 in production medium is produced on a 60-conical-flask scale with addition at 16 hours of 1 ml of a solution containing 10 g/l of (R,S)-3-fluoro-4-methylphenyl-alanine in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in di-chloromethane. The fractions containing the novel pristinamycin $I_a$ derivative are pooled and evaporated. 15 mg of dry residue are obtained. This residue is taken up in 3 ml of a 60% water and 40% acetonitrile mixture and is injected onto a Nucleosil 7μ C8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 9 mg of 4-ε-fluoro-4-ζ-methylde(4-ζ-dimethylamino)pristinamycin $I_A$ are obtained.

$^1$H NMR spectrum (400 MHz, CDCl$_3$, δ in ppm, ref. TMS): 0.60 (dd, J=16 and 5.5 Hz , 1H: 5 β$_2$), 0.91 (t, J=7.5 Hz , 3H: CH$_3$ 2 γ), 1.12 (mt, 1H: 3 β$_2$), from 1.25 to 1.35 (mt, 1H: 3 γ$_2$), 1.33 (d, J=7.5 Hz , 3H: CH$_3$ 1 γ), from 1.50 to 1.85 (mt, 3H: 3 γ$_1$ and CH$_2$ 2 β), 2.02 (mt, 1H: 3 β$_1$), 2.13 (mt, 1H: 5 δ$_2$), 2.27 (s, 3H: ArCH$_3$), 2.36 (broad d, J=16 Hz , 1H: 5 δ$_1$), 2.45 (d, J=16 Hz, 1H: 5 β$_1$), 2.85 (dt, J=13 and 4.5 Hz , 1H: 5 ε$_2$), 2.97 (dd, J=12.5 and 4.5 Hz , 1H: 4 β$_2$), 3.23 (s, 3H: NCH$_3$ 4), 3.30 and 3.56 (2 mts, 1H each: CH$_2$ 3 δ), 3.37 (t, J=12.5 Hz , 1H: 4 β$_1$), 4.55 (t, J=7.5 Hz , 1H: 3 α), 4.75 (broad dd, J=13 and 8 Hz , 1H: 5 ε$_1$), 4.83 (mt, 1H: 2α), 4.89 (broad d, J=10 Hz , 1H: 1α), 5.29 (dd, J=12.5 and 4.5 Hz , 1H: 4 α), 5.32 (broad d, J=5.5 Hz , 1H: 5 α), 5.89 (d, J=9.5 Hz , 1H: 6 α), 5.92 (mt, 1H: 1β), 6.49 (d, J=10 Hz , 1H: NH 2), 6.90 (mt, 2H: H 2 and H 6 of the aromatic at 4), 7.11 (t, J=8 Hz , 1H: H 5 of the aromatic at 4), from 7.10 to 7.30 (mt, 5H: aromatic H at 6), 7.43 (dd, J=8.5 and 1 Hz , 1H: 1' H$_4$), 7.49 (dd, J=8.5 and 4.5 Hz , 1H: 1' H$_5$), 7.75 (dd, J=4.5 and 1 Hz , 1H: 1' H$_6$), 8.48 (d, J=10 Hz , 1H: NH 1), 8.70 (d, J=9.5 Hz, 1H: NH 6), 11.60 (s, 1H: OH).

The (R,S)-3-fluoro-4-methylphenylalanine hydrochloride may be prepared in the following way:

12 N hydrochloric acid is added to 1.6 g of methyl N-acetyl(3-fluoro-4-methyl)phenylalaninate and the mixture is heated at reflux with stirring for 8 hours. After one night at room temperature, the reaction mixture is concentrated to dryness under reduced pressure (50 kPa) and taken up in a 50/50 by volume mixture of toluene and ethanol and then concentrated to dryness again. After drying under reduced pressure (2.6 kPa), 0.6 g of (R,S)-3-fluoro-4- methylphenylalanine hydrochloride is obtained in the form of white crystals melting at a temperature above 260° C.

The methyl (R,S)-N-acetyl(3-fluoro-4-methyl)-phenylalaninate may be prepared in the following way:

0.2 g of 10% palladium-on-charcoal in 230 ml of absolute ethanol is added to 1.9 g of methyl 2-(4-methyl-3-fluoro) acetamidocinnamate placed under a nitrogen atmosphere in an autoclave. The mixture is placed under a pressure of 5.5 bar of hydrogen and heated at 50° C. for 15 hours with stirring. After stabilizing the temperature to 26° C. and returning to atmospheric pressure, the reaction mixture is filtered through Clarcel®, rinsed with ethanol and then concentrated to dryness under reduced pressure (2.6 kPa). 1.6 g of methyl N-acetyl(3-fluoro-4-methyl)-phenylalaninate are obtained in the form of a colourless oil (Merck Silica 5719, Rf=0.46; 50/50 $CH_2Cl_2$/EtOAc eluent).

The methyl 2-(3-fluoro-4-methyl)acetamidocinnamate may be prepared in the following way:

3.6 g of methyl 2-acetamidoacrylate, 0.12 g of palladium acetate, 5.2 g of tetrabutylammonium chloride and 3.8 g of sodium hydrogen carbonate are added to a three-necked flask placed under nitrogen, followed by addition to this mixture of 4 g of 2-fluoro-4-bromotoluene dissolved in 120 ml of anhydrous DMF. The mixture is heated at 82° C. for 16 hours 30 minutes and, after cooling, is then poured into 1000 ml of distilled water. The mixture is taken up in 250 ml of $CH_2Cl_2$, the organic phase is separated out after settling has taken place and the aqueous phase is washed with twice 250 ml of $CH_2Cl_2$. The organic phases are combined, dried over sodium sulphate, filtered and concentrated under reduced pressure (50 kPa) at 70° C. to give a brown oil which is purified by flash chromatography (eluent: EtOAc/cyclohexane and then pure EtOAc). 2.6 g of methyl 2-(3-fluoro-4-methyl)acetamidocinnamate are obtained in the form of a white solid melting at 163° C.

EXAMPLE O

Preparation of 4-ε-ethoxyde(4-ζ-dimethylamino)pristinamycin $I_A$

As described in Example F, a culture of the strain SP92::pVRC508 in production medium is produced on a 60-conical-flask scale with addition at 16 hours of 1 ml of a solution containing 20 g/l of (R,S)-3-O-ethyltyrosine hydrochloride in 0.2N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. 19 mg of dry residue are obtained. This residue is taken up in 3 ml of a 60% water and 40% acetonitrile mixture and is injected onto a Nucleosil 7μ C8 10×250 mm semi-preparative column (Macherey Nagel) eluted with a mixture of 60% 100 mM phosphate buffer pH 2.9 and 40% acetonitrile. The fractions containing the novel pristinamycin are pooled and extracted with one volume of dichloromethane. The organic phase is washed with water, dried over sodium sulphate and then evaporated. 15.8 mg of 4-ε-ethoxyde(4-ζ-dimethylamino)pristinamycin $I_A$, are obtained.

$^1$H NMR spectrum (400 MHz, $CDCl_3$, δ in ppm, ref. TMS): 0.55 (dd, J=16 and 5.5 Hz , 1H: 1H of the $CH_2$ at 5 1β); 0.90 (t, J=7.5 Hz , 3H: $CH_3$ at 2 γ); 1.12 (mt, 1H: 1H of the $CH_2$ at 3 β); 1.20 (mt, 1H: 1H of the $CH_2$ at 3 γ); 1.31 (d, J=6.5 Hz , 3H: $CH_3$ at 1 γ); 1.49 (t, J=7 Hz , 3H: $CH_3$ of the ethyl); 1.54 (mt, 1H: other H of the $CH_2$ at 3 γ); 1.63 and 1.73 (2 mts, 1H each: $CH_2$ at 2 β); 2.02 (mt, 1H: other H of the $CH_2$ at 3 β); 2.22 and 2.33 (mt and broad d respectively, J=16.5 Hz , 1H each: $CH_2$ at 5 δ); 2.46 (d, J=16 Hz , 1H: other H of the $CH_2$ at 5 β); 2.83 (dt, J=13 and 4 Hz , 1H: 1H of the $CH_2$ at 5 ε); 2.95 (dd, J=12 and 4 Hz , 1H: 1H of the $CH_2$ at 4 β); 3.22 (mt, 1H: 1H of the $CH_2$ at 3 δ); 3.27 (s, 3H: $NCH_3$); 3.39 (t, J=12 Hz , 1H: other H of the $CH_2$ at 4 β); 3.53 (mt, 1H: other H of the $CH_2$ at 3 δ); 3.93 and 4.03 (2 mts, 1H each: $OCH_2$ of the ethyl); 4.56 (dd, J=7 and 5.5 Hz , 1H: 3 α); 4.75 (broad dd, J=13 and 8 Hz , 1H: other H of the $CH_2$ at 5 ε); 4.82 (mt, 1H: 2 α); 4.88 (dd, J=10 and 1 Hz , 1H: 1 α); 5.23 (dd, J=12 and 4 Hz, 1H: 4 α); 5.23 (broad d, J=5.5 Hz, 1H: 5 α); 5.87 (d, J=9.5 Hz, 1H: 6 α); 5.92 (mt, 1H: 1 β); 6.47 (d, J=10 Hz, 1H: NH at 2); 6.80 (mt, 3H: aromatic H ortho and para to the ethoxy); from 7.10 to 7.35 (mt, 6H: aromatic H at 6 and aromatic H meta to the ethoxy); 7.43 (dd, J=8 and 1 Hz, 1H: 1' $H_4$); 7.50 (dd, J=8 and 4 Hz, 1H: 1' $H_5$); 7.77 (dd, J=4 and 1 Hz, 1H: 1' $H_6$); 8.38 (d, J=10 Hz, 1H: NH at 1); 8.70 (d, J=9.5 Hz, 1H: NH at 6); 11.60 (s, 1H: OH).

The (R,S)-3-O-ethyltyrosine hydrochloride may be prepared in the following way:

1 g of (R,S)-N-tert-butoxycarbonyl-3-ethoxy-phenylalanine dissolved in 3.6 ml of hydrochloric dioxane is placed in a round-bottomed flask and the mixture is then stirred at room temperature for 5 hours. The precipitate formed is filtered off, rinsed with dioxane and then with ether and then dried under reduced pressure (2.7 kPa) at 40° C. to give 0.65 g of (R,S)-3-O-ethyltyrosine hydrochloride in the form of a white solid melting at 200° C.

The (R,S)-N-tert-butoxycarbonyl-3-ethoxy-phenylalanine may be prepared in the following way:

1.33 g of ethyl (R,S)-N-tert-butoxycarbonyl-3-ethoxyphenylalaninate dissolved in 8 ml of methanol are placed in a round-bottomed flask and 8 ml of 1N sodium hydroxide are then added. After stirring at room temperature for 18 hours, the mixture is evaporated under reduced pressure and then acidified with 8.56 ml of 1N hydrochloric acid. The product is extracted with twice 10 ml of ethyl acetate and the organic phases are combined, washed with twice 10 ml of water, dried, filtered and then concentrated to dryness under reduced pressure to give 1 g of (R,S)-N-tert-butoxycarbonyl-3-ethoxyphenylalanine in the form of a yellow oil (Merck Silica 5719, Rf=0.7, eluent: 80 toluene/10 MeOH/10 diethylamine).

The ethyl (R,S)-N-tert-butoxycarbonyl-3-ethoxyphenylalaninate may be prepared in the following way:

1.5 g of (R,S)-N-tert-butoxycarbonyl-3-tyrosine dissolved in 7.5 ml of dry dimethylformamide are placed in a three-necked flask under a nitrogen atmosphere and 0.508 g of 50% sodium hydride in oil is then added. After stirring for 2 hours at room temperature, 0.86 ml of iodoethane is added and the mixture is then stirred for 4 hours at room temperature. The medium is filtered and the resulting solid is washed with 3 times 10 ml of water and then twice 10 ml of petroleum ether to give, after drying under reduced pressure (2.7 kPa) at 30° C., 1.33 g of ethyl (R,S)-N-tert-butoxycarbonyl-3-ethoxyphenyl-alaninate in the form of a white solid.

The (R,S)-N-tert-butoxycarbonyl-3-tyrosine may be prepared in the following way:

18 g of (R,S)-3-tyrosine dissolved in 180 ml of dioxane are placed in a three-necked flask with stirring and 99 ml of 1N sodium hydroxide are then added, followed by 26 g of di-tert-butyl dicarbonate dissolved in 160 ml of dioxane. After stirring for 36 hours, the medium is concentrated under reduced pressure at 30° C., taken up in 100 ml of distilled water, acidified with 1N hydrochloric acid to pH 5 and then extracted with twice 200 ml of ethyl acetate. The organic phase is dried over magnesium sulphate, filtered and then concentrated to dryness under reduced pressure at 30° C. to give 30 g of (R,S)-N-tert-butoxycarbonyl-3-tyrosine in the form of a white solid (Merck Silica 5719, Rf=0.25, eluent: 80 toluene/10 MeOH/10 diethylamine).

EXAMPLE P

Preparation of 4-ζ-ethoxyde(4-ζ-dimethylamino) pristinamycin $I_A$

As described in Example F, a culture of the strain SP92::pVRC508 in production medium is produced on a 90-conical-flask scale with addition at 16 hours of 1 ml of a solution containing 20 g/l of (S)-4-O-ethyltyrosine hydrochloride in 0.1N hydrochloric acid. After culturing for 40 hours, the 2.7 liters of broth obtained from the 90 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the 4-ζ-ethoxyde(4-ζ-dimethylamino) pristinamycin $I_A$ are pooled and evaporated. The dry residue is taken up in 7 ml of a 60% water and 40% acetonitrile mixture and is injected onto a Nucleosil 7μ C8 10×250 mm semi-preparative column (Macherey Nagel) eluted with a mixture of 52% 100 mM phosphate buffer pH 2.9 and 48% acetonitrile. The fractions containing the 4-ζ-ethoxyde(4-ζ-dimethylamino)pristinamycin $I_A$ are pooled and extracted with one volume of dichloromethane. The organic phase is washed with water, dried over sodium sulphate and then evaporated. 29 mg of 4-ζ-ethoxyde(4-ζ-dimethylamino) pristinamycin $I_A$ are obtained.

$^1$H NMR spectrum (400 MHz, CDCl$_3$, δ in ppm, ref. TMS): 0.64 (dd, J=16 and 5.5 Hz, 1H: 1H of the CH$_2$ at 5 β); 0.90 (t, J=7.5 Hz, 3H: CH$_3$ at 2 γ); 1.12 (mt, 1H: 1H of the CH$_2$ at 3 β); 1.25 (mt, 1H: 1H of the CH$_2$ at 3 γ); 1.33 (d, J=7 Hz, 3H: CH$_3$ at 1 γ); 1.42 (t, J=7 Hz, 3H: CH$_3$ of the ethyl); 1.57 (mt, 1H: other H of the CH$_2$ at 3 γ); 1.63 and 1.74 (2 mts, 1H each: CH$_2$ at 2 β); 2.02 (mt, 1H: other H of the CH$_2$ at 3 β); 2.16 and 2.35 (mt and broad d respectively, J=16.5 Hz, 1H each: CH$_2$ at 5 δ); 2.43 (d, J=16 Hz, 1H: other H of the CH$_2$ at 5 β); 2.83 (dt, J=13 and 4 Hz, 1H: 1H of the CH$_2$ at 5 ε); 2.93 (dd, J=12 and 4 Hz, 1H: 1H of the CH$_2$ at 4 β); from 3.15 to 3.30 (mt, 1H: 1H of the CH$_2$ at 3 δ); 3.24 (s, 3H: NCH$_3$); 3.35 (t, J=12 Hz, 1H: other H of the CH$_2$ at 4 β); 3.55 (mt, 1H: other H of the CH$_2$ at 3 δ); 3.95 (limiting AB, 2H: OCH$_2$ of the ethyl); 4.56 (dd, J=7.5 and 6 Hz, 1H: 3 α); 4.75 (broad dd, J=13 and 8 Hz, 1H: other H of the CH$_2$ at 5 ε); 4.84 (mt, 1H: 2 α); 4.87 (dd, J=10 and 1 Hz, 1H: 1 α); 5.26 (dd, J=12 and 4 Hz, 1H: 4 α); 5.32 (broad d, J=5.5 Hz, 1H: 5 α); 5.88 (d, J=10 Hz, 1H: 6 α); 5.92 (mt, 1H: 1 β); 6.48 (d, J=10 Hz, 1H: NH at 2); 6.83 (d, J=8 Hz, 2H: aromatic H at 4 ε); 7.10 (d, J=8 Hz, 2H: aromatic H at 4 δ); from 7.10 to 7.35 (mt, 5H aromatic H at 6); 7.44 (dd, J=8.5 and 1.5 Hz, 1H: 1' H$_4$); 7.57 (dd, J=8.5 and 4.5 Hz, 1H: 1' H$_5$); 7.77 (dd, J=4.5 and 1.5 Hz, 1H: 1' H$_6$); 8.38 (d, J=10 Hz, 1H: NH at 1); 8.75 (d, J=10 Hz, 1H: NH at 6); 11.60 (s, 1H: OH).

The (S)-4-O-ethyltyrosine hydrochloride may be synthesized as described by Y. Sasaki et al., Chem. Pharm. Bull., 30, 4435 (1982).

EXAMPLE Q

Preparation of 4-ζ-allyloxyde(4-ζ-dimethylamino) pristinamycin $I_A$

As described in Example F, a culture of the strain SP92::pVRC508 in production medium is produced on a 90-conical-flask scale with addition at 16 hours of 1 ml of a solution containing 20 g/l of (S)-4-O-allyltyrosine hydrochloride in 0.1N hydrochloric acid. After culturing for 40 hours, the 2.7 liters of broth obtained from the 90 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the 4-ζ-allyloxyde(4-ζ-dimethylamino) pristinamycin $I_A$ are pooled and evaporated. The dry residue is taken up in 7 ml of a 60% water and 40% acetonitrile mixture and is injected onto a Nucleosil 7μ C8 10×250 mm semi-preparative column (Macherey Nagel) eluted with a mixture of 52% 100 mM phosphate buffer pH 2.9 and 48% acetonitrile. The fractions containing the 4-70 -allyloxyde (4-ζ-dimethylamino)pristinamycin $I_A$ are pooled and extracted with one volume of dichloromethane. The organic phase is washed with water, dried over sodium sulphate and then evaporated. 29 mg of 4-ζ-allyloxyde(4-ζ-dimethylamino)pristinamycin $I_A$ are obtained.

$^1$H NMR spectrum (400 MHz, CDCl$_3$, δ in ppm, ref. TMS): 0.63 (dd, J=16 and 6 Hz, 1H: 1H of the CH$_2$ at 5 β); 0.91 (t, J=7.5 Hz, 3H: CH$_3$ at 2 γ); 1.13 (mt, 1H: 1H of the CH$_2$ at 3 β); 1.29 (mt, 1H: 1H of the CH$_2$ at 3 γ); 1.33 (d, J=6.5 Hz, 3H: CH$_3$ at 1 γ); 1.57 (mt, 1H: other H of the CH$_2$ at 3 γ); 1.65 and 1.74 (2 mts, 1H each: CH$_2$ at 2 β); 2.02 (mt, 1H: other H of the CH$_2$ at 3 β); 2.14 and 2.34 (mt and broad d respectively, J=16.5 Hz, 1H each: CH$_2$ at 5 δ); 2.43 (d, J=16 Hz, 1H: other H of the CH$_2$ at 5 β); 2.85 (dt, J=13 and 4 Hz, 1H: 1H of the CH$_2$ at 5 ε); 2.95 (dd, J=12 and 4 Hz, 1H: 1H of the CH$_2$ at 4 β); 3.25 (s, 3H: NCH$_3$); 3.33 (mt, 1H: 1H of the CH$_2$ at 3 δ); 3.36 (t, J=12 Hz, 1H: other H of the CH$_2$, at 4 β); 3.56 (mt, 1H: other H of the CH$_2$ at 3 δ); 4.51 (limiting AB, 2H: OCH$_2$ of the allyl); 4.56 (t, J=7.5 Hz, 1H: 3 α); 4.75 (broad dd, J=13 and 8 Hz, 1H: other H of the CH$_2$ at 5 ε); 4.84 (mt, 1H: 2 α); 4.88 (dd, J=10 and 1 Hz, 1H: 1 α); 5.27 (dd, J=12 and 4 Hz, 1H: 4 α); 5.32 (broad d, J=6 Hz, 1H: 5 α); 5.30 and 5.40 (mt and d respectively, J=17 and 1.5 Hz, 1H each: =CH$_2$ of the allyl); 5.89 (d, J=9.5 Hz, 1H: 6 α); 5.91 (mt, 1H: 1 β); 6.02 (mt, 1H: CH= of the allyl); 6.50 (d, J=10 Hz, 1H: NH at 2); 6.85 (d, J=8 Hz, 2H: aromatic H at 4 ε); 7.12 (d, J=8 Hz, 2H: aromatic H at 4 δ); from 7.10 to 7.35 (mt, 5H: aromatic H at 6); 7.45 (d, J=8.5 and 1.5 Hz, 1H: 1' H$_4$); 7.57 (dd, J=8.5 and 4 Hz, 1H: 1' H$_5$); 7.77 (dd, J=4 and 1.5 Hz, 1H: 1' H$_6$); 8.41 (d, J=10 Hz, 1H: NH at 1); 8.74 (d, J=9.5 Hz, 1H: NH at 6); 11.63 (s, 1H: OH).

The (S)-4-O-allyltyrosine hydrochloride may be synthesized as described by A. Loffet, H. Zang, Int. J. Pept. Protein Res., 42, 346 (1993).

EXAMPLE R

Preparation of 4-ζ-ethylaminode(4-ζ-dimethylamino) pristinamycin $I_A$

As described in Example F, a culture of the strain SP92::pVRC508 in production medium is produced on a 50-conical-flask scale with addition at 16 hours of 1 ml of a solution containing 20 g/l of (R,S)-4-ethylaminophenylalanine dihydrochloride in 0.1N sodium hydroxide. After culturing for 40 hours, the 1.5 liters of broth obtained from the 50 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the 4-ζ-ethylaminode(4-ζ-dimethylamino)pristinamycin $I_A$ are pooled and evaporated. The dry residue is taken up in 7 ml of a 65% water and 35% acetonitrile mixture and is injected onto a Nucleosil 7μ C8 10×250 mm semi-preparative column (Macherey Nagel) eluted with a mixture of 60% 100 mM phosphate buffer pH 2.9 and 40% acetonitrile. The fractions containing the 4-ζ-ethylaminode(4-ζ-dimethylamino)pristinamycin $I_A$ are pooled and extracted with one volume of dichloromethane. The organic phase is washed with water, dried over sodium sulphate and then evaporated. 10 mg of 4-ζ-ethylaminode (4-ζ-dimethylamino)pristinamycin $I_A$ are obtained.

$^1$H NMR spectrum (400 MHz, CDCl₃, δ in ppm, ref. TMS): 0.72 (dd, J=16 and 6 Hz, 1H: 1H of the CH₂ at 5 β); 0.90 (t, J=7.5 Hz, 3H: CH₃ at 2 γ); 1.15 (mt, 1H: 1H of the CH₂ at 3 β); from 1.20 to 1.40 (mt, 1H: 1H of the CH₂ at 3 γ); 1.27 (t, J=7.5 Hz, 3H: CH₃ of the ethyl); 1.33 (d, J=7 Hz, 3H: CH₃ at 1 γ); from 1.50 to 1.65 (mt, 1H: other H of the CH₂ at 3 γ); 1.60 and 1.74 (2 mts, 1H each: CH₂ at 2 β); 2.02 (mt, 1H: other H of the CH₂ at 3 β); 2.21 and 2.33 (mt and broad d respectively, J=16.5 Hz, 1H each: CH₂ at 5 δ); 2.40 (d, J=16 Hz, 1H: other H of the CH₂ at 5 β); 2.82 (dt, J=13 and 4.5 Hz, 1H: 1H of the CH₂ at 5 ε); 2.89 (dd, J=12 and 4 Hz, 1H: 1H of the CH₂ at 4 β); 3.10 (mt, 2H: NCH₂ of the ethyl); from 3.20 to 3.35 (mt, 1H: 1H of the CH₂ at 3 δ); 3.26 (s, 3H: NCH₃); 3.31 (t, J=12 Hz, 1H: other H of the CH₂ at 4 β); 3.54 (mt, 1H: other H of the CH₂ at 3 δ); 3.67 (unres. mult., 1H: NH); 4.56 (dd, J=6.5 and 7 Hz, 1H: 3 α); 4.75 (broad dd, J=13 and 8 Hz, 1H: other H of the CH₂ at 5 ε); 4.84 (mt, 2 α); 4.90 (broad d, J=10 Hz, 1H: 1 α); 5.24 (dd, J=12 and 4 Hz, 1H: 4 α); 5.32 (broad d, J=6 Hz, 1H: 5 α); 5.88 (d, J=9.5 Hz, 1H: 6 α); 5.90 (mt, 1H: 1 β); 6.52 (d, J=8 Hz, 3H: NH at 2 and aromatic H at 4 ε); 7.00 (d, J=8 Hz, 2H: aromatic H at 4 δ); from 7.10 to 7.35 (mt, 5H: aromatic H at 6); 7.46 (limiting AB, 2H: 1' H₄ and 1' H₅); 7.84 (dd, J=4 and 1 Hz, 1H: 1' H₆); 8.45 (d, J=10 Hz, 1H: NH at 1); 8.77 (d, J=9.5 Hz, 1H: NH at 6); 11.65 (s, 1H: OH).

The (R,S)-4-ethylaminophenylalanine dihydrochloride may be prepared according to the method described by F. Bergel, J. A. Stock, J. Chem. Soc. 90–97 (1959).

EXAMPLE S

Preparation of 4-ζ-trifluoromethoxyde(4-ζ-dimethylamino) pristinamycin $I_A$

As described in Example F, a culture of the strain SP92::pVRC508 in production medium is produced on a 60-conical-flask scale with addition at 16 hours of 1 ml of a solution containing 20 g/l of (R,S)-4-O-trifluoromethyltyrosine hydrochloride in water. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in dichloromethane and injected onto a column of silica (30 g) mounted in dichloromethane and eluted successively with levels of from 0 to 10% methanol in dichloromethane. The fractions containing the 4-ζ-trifluoromethoxyde(4-ζ-dimethylamino)pristinamycin $I_A$ are pooled and evaporated. The dry residue is taken up in 7 ml of a 60% water and 40% acetonitrile mixture and is injected onto a Nucleosil 7μ C8 10×250 mm semi-preparative column (Macherey Nagel) eluted with a mixture of 60% 100 mM phosphate buffer pH 2.9 and 40% acetonitrile. The fractions containing the 4-ζ-trifluoromethoxyde(4-ζ-dimethylamino)pristinamycin $I_A$ are pooled and extracted with one volume of dichloromethane. The organic phase is washed with water, dried over sodium sulphate and then evaporated. 46.5 mg of 4-ζ-trifluoromethoxyde(4-ζ-dimethylamino)pristinamycin $I_A$ are obtained.

$^1$H NMR spectrum (400 MHz, CDCl₃, δ in ppm, ref. TMS): 0.77 (dd, J=16 and 5.5 Hz, 1H: 1H of the CH₂ at 5 β); 0.92 (t, J=7.5 Hz, 3H: CH₃ at 2 γ); 1.08 (mt, 1H: 1H of the CH₂ at 3 β); from 1.30 to 1.40(mt, 1H: 1H of the CH₂ at 3 γ); 1.33 (d, J=7 Hz, 3H: CH₃ at 1 γ); from 1.55 to 1.70 (mt, 1H: other H of the CH₂ at 3 γ); 1.65 and 1.76 (2 mts, 1H each: CH₂ at 2 β); 2.02 (mt, 1H: other H of the CH₂ at 3 β); 2.11 and 2.40 (mt and broad d respectively, J=16.5 Hz, 1H each: CH₂ at 5 δ); 2.54 (d, J=16 Hz, 1H: other H of the CH₂ at 5 β); 2.88 (dt, J=13 and 4 Hz, 1H: 1H of the CH₂ at 5 ε); 3.08 (dd, J=12 and 5 Hz, 1H: 1H of the CH₂ at 4 β); 3.22 (s, 3H: NCH₃); from 3.30 to 3.45 (mt, 1H: 1H of the CH₂ at 3 δ); 3.39 (t, J=12 Hz, 1H: other H of the CH₂ at 4 β); 3.59 (mt, 1H: other H of the CH₂ at 3 δ); 4.53 (t, J=7.5 Hz, 1H: 3 α); 4.75 (broad dd, J=13 and 8 Hz, 1H: other H of the CH₂ at 5 ε); 4.85 (mt, 1H: 2 α); 4.89 (dd, J=10 and 1.5 Hz, 1H: 1 α); 5.35 (broad d, J=5.5 Hz, 1H: 5 α); 5.41 (dd, J=12 and 5 Hz, 1H: 4 α); 5.92 (d, J=10 Hz, 1H: 6 α); 5.93 (mt, 1H: 1 β); 6.53 (d, J=9.5 Hz, 1H: NH at 2); from 7.15 to 7.35 (mt, 5H: aromatic H at 6); 7.16 (d, J=8 Hz, 2H: aromatic H at 4 ε); 7.26 (d, J=8 Hz, 2H: aromatic H at 4 δ); 7.37 (dd, J=8.5 and 4 Hz, 1H: 1' H₅); 7.42 (dd, J=8.5 and 1.5 Hz, 1H: 1' H₄); 7.70 (dd, J=4 and 1.5 Hz, 1H: 1' H₆); 8.37 (d, J=10 Hz, 1H: NH at 1); 8.75 (d, J=10 Hz, 1H: NH at 6); 11.66 (s, 1H: OH).

The (R,S)-4-O-trifluoromethyltyrosine hydrochloride may be prepared in the following way:

Working as in Example N, but starting with 3 g of methyl N-acetyl (4-trifluoromethoxy)phenylalaninate and 30 ml of 12N hydrochloric acid, 1.5 g of (R,S)-4-O-trifluoromethyltyrosine hydrochloride are obtained in the form of white crystals melting at 260° C.

The methyl (R,S)-N-acetyl(4-trifluoromethoxy) phenylalaninate may be prepared in the following way:

Working as in Example N, but starting with 3.1 g of methyl 2-(4-trifluoromethoxy)acetamidocinnamate and 0.3 g of 10% palladium-on-charcoal in 50 ml of ethanol, 3 g of methyl N-acetyl(4-trifluoromethoxy)phenylalaninate are obtained in the form of a white solid melting at 80° C.

The methyl 4-trifluoromethoxy-2-acetamidocinnamate may be prepared in the following way:

Working as in Example N, but starting with 4.3 g of methyl 2-acetamidoacrylate, 0.14 g of palladium acetate, 6.1 g of tetrabutylammonium chloride, 4.6 g of sodium hydrogen carbonate and 5 g of 4-trifluoromethoxybromobenzene dissolved in 150 ml of of anhydrous dimethylformamide, 3.1 g of methyl 2-(4-trifluoromethoxy)acetamidocinnamate are obtained in the form of a white solid melting at 135° C.

EXAMPLE T

Preparation of 4-ε-methylthiode(4-ζ-dimethylamino) pristinamycin $I_A$

As described in Example F, a culture of the strain SP92::pVRC508 in production medium is produced on a 56-conical-flask scale with addition at 16 hours of 1 ml of a solution containing 20 g/l of (R,S)-3-methylthiophenylalanine hydrochloride in 0.1N sodium hydroxide. After culturing for 40 hours, the 1.68 liters of broth obtained from the 56 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the novel pristinamycin $I_A$ derivative are pooled and evaporated. The dry residue is taken up in 7 ml of a 54% water and 46% acetonitrile mixture and is injected onto a Nucleosil 7μC8 10×250 mm semi-preparative column (Macherey Nagel) eluted with a mixture of 55% 100 mM phosphate buffer pH 2.9 and 45% acetonitrile. The fractions containing the novel pristinamycin are pooled and extracted with one volume of dichloromethane. The organic phase is washed with water, dried over sodium sulphate and then evaporated. 20 mg of 4-ε-methylthiode (4-ζ-dimethylamino)pristinamycin $I_A$ are obtained.

$^1$H NMR spectrum (400 MHz, CDCl$_3$, δ in ppm, ref. TMS): 0.56 (dd, J=16 and 5.5 Hz, 1H: 1H of the CH$_2$ at 5 β); 0.90 (t, J=7.5 Hz, 3H: CH$_3$ at 2 γ); 1.13 (mt, 1H: 1H of the CH$_2$ at 3 β); 1.28 (mt, 1H: 1H of the CH$_2$ at 3 γ); 1.32 (d, J=6.5 Hz, 3H: CH$_3$ at 1 γ); 1.58 (mt, 1H: other H of the CH$_2$ at 3 γ); 1.62 and 1.74 (2 mts, 1H each: CH$_2$ at 2 β); 2.02 (mt, 1H: other H of the CH$_2$ at 3 β); 2.25 and 2.35 (mt and broad d respectively, J=16.5 Hz, 1H each: CH$_2$ at 5 δ); 2.39 (d, J=16 Hz, 1H: other H of the CH$_2$ at 5 β); 2.43 (s, 3H: SCH$_3$); 2.82 (dt, J=13 and 4 Hz, 1H: 1H of the CH$_2$ at 5 ε); 2.98 (dd, J=12 and 4.5 Hz, 1H: 1H of the CH$_2$ at 4 β); 3.26 (s, 3H. NCH$_3$); 3.30 (t, J=12 Hz, 1H: 1H of the CH$_2$ at 3 δ); 3.38 (mt, 1H: other H of the CH$_2$ at 4 β); 3.57 (mt, 1H: other H of the CH$_2$ at 3 δ); 4.56 (t, J=7.5 Hz, 1H: 3 α); 4.74 (broad dd, J=13 and 8 Hz, 1H: other H of the CH$_2$ at 5 ε); 4.84 (mt, 1H: 2 α); 4.89 (dd, J=10 and 1 Hz, 1H: 1 α); 5.29 (dd, J=12 and 4.5 Hz, 1H: 4 α); 5.32 (broad d, J=5.5 Hz, 1H: 5 α); 5.88 (d, J=9.5 Hz, 1H: 6 α); 5.90 (mt, 1H: 1 β); 6.51 (d, J=10 Hz, 1H: NH at 2); 6.99 (broad d, J=8 Hz, 1H: aromatic H para to the methylthio); 7.10 and 7.15 (broad s and broad d respectively, J=8 Hz, 1H each: aromatic H ortho to the methylthio; from 7.15 to 7.35 (mt, 6H: aromatic H at 6 and aromatic H meta to the methylthio; 7.43 (broad d, J=8 Hz, 1H: 1' H$_4$); 7.52 (dd, J=8 and 4 Hz, 1H: 1' H$_5$); 7.79 (broad d, J=4 Hz, 1H: 1' H$_6$); 8.38 (d, J=10 Hz, 1H: NH at 1); 8.73 (d, J=9.5Hz, 1H: NH at 6); 11.62 (s, 1H: OH).

The (R,S)-3-methylthiophenylalanine hydrochloride may be prepared in the following way:

Working as in Example N, but starting with 3.3 g of methyl N-acetyl-3-methylthiophenylalaninate and 40 ml of 12N hydrochloric acid, 1.38 g of (R,S)-3-methylthiophenylalanine hydrochloride are obtained in the form of white crystals melting at 190° C.

The methyl (R,S)-N-acetyl-3-methylthiophenylalaninate may be prepared in the following way:

3.72 g of methyl 3-methylthio-2-acetamidocinnamate dissolved in 100 ml of methanol and 30 ml of tetrahydrofuran are placed in a round-bottomed flask and 1.4 g of magnesium are then added. After reacting for 20 minutes, the mixture is cooled in an ice bath and a further 1.4 g of magnesium are added. The mixture is stirred at room temperature for 18 hours, poured into 1.4 l of distilled water and 300 ml of CH$_2$Cl$_2$ and then filtered through Clarcel®. The aqueous phase is adjusted to pH 6 by addition of 12N hydrochloric acid and is then separated out after settling of the phases has taken place and washed with 100 ml of CH$_2$Cl$_2$. The organic phases are combined, dried over magnesium sulphate, filtered and then concentrated to dryness under reduced pressure to give 3.42 g of methyl N-acetyl-3-methylthiophenylalaninate in the form of a colourless oil (Merck Silica 5719, Rf=0.5; EtOAc).

The methyl 3-methylthio-2-acetamidocinnamate may be prepared in the following way:

Working as in Example N, but starting with 5.6 g of methyl 2-acetamidoacrylate, 0.18 g of palladium acetate, 8.2 g of tetrabutylammonium chloride, 5.86 g of sodium hydrogen carbonate and 6.5 g of 3-iodo-1-methylthiobenzene dissolved in 160 ml of anhydrous dimethylformamide, 4.8 g of methyl 2-(3-methylthio)acetamidocinnamate are obtained in the form of a white solid melting at 139° C.

EXAMPLE U

Preparation of 4-ζ-(allylethylamino)de(4-ζ-dimethylamino) pristinamycin $I_A$

As described in Example F, a culture of the strain SP92::pVRC508 in production medium is produced on a 26-conical-flask scale with addition at 16 hours of 1 ml of a solution containing 20 g/l of (R,S)-4-(allylethylamino) phenylalanine dihydrochloride in 0.1N sodium hydroxide. After culturing for 40 hours, the 0.78 liter of broth obtained from the 26 flasks is extracted with 2 volumes of a mixture of 66% 100 mM phosphate buffer pH 2.9 and 34% acetonitrile and is then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the 4-ζ-(allylethylamino)de(4-ζ-dimethylamino)pristinamycin $I_A$ are pooled and evaporated. The dry residue is taken up in 7 ml of a 60% water and 40% acetonitrile mixture and is injected onto a Nucleosil 7μ C8 10×250 mm semi-preparative column (Macherey Nagel) eluted with a mixture of 52% 100 mM phosphate buffer pH 2.9 and 48% acetonitrile. The fractions containing the 4-ζ-(allylethylamino)de (4-ζ-dimethylamino)pristinamycin $I_A$ are pooled and extracted with one volume of dichloromethane. The organic phase is washed with water, dried over sodium sulphate and then evaporated. 20 mg of 4-ζ-(allylethylamino)de(4-ζ-dimethylamino)pristinamycin $I_A$ are obtained.

$^1$H NMR spectrum (400 MHz, CDCl$_3$, δ in ppm, ref. TMS) 0.58 (dd, J=16 and 6 Hz, 1H: 1H of the CH$_2$ at 5 β); 0.91 (t, J=7.5 Hz, 3H: CH$_3$ at 2 γ); 1.16 (t, J=7 Hz, 3H: CH$_3$ of the ethyl; 1.16 (mt, 1H: 1H of the CH$_2$ at 3 β); 1.25 (mt, 1H: 1H of the CH$_2$ at 3 γ); 1.32 (d, J=6.5 Hz, 3H: CH$_3$ at 1 γ); 1.54 (mt, 1H: other H of the CH$_2$ at 3 γ); 1.63 and 1.75 (2 mts, 1H each: CH$_2$ at 2 β); 2.02 (mt, 1H: other H of the CH$_2$ at 3 β); 2.23 and 2.31 (mt and broad d respectively, J=16.5 Hz, 1H each: CH$_2$ at 5 δ); 2.37 (d, J=16 Hz, 1H: other H of the CH$_2$ at 5 β); 2.80 (dt, J=13 and 4.5 Hz, 1H: 1H of the CH$_2$ at 5 ε); 2.87 (dd, J=12 and 4 Hz, 1H: 1H of the CH$_2$ at 4 β); from 3.15 to 3.30 (mt, 1H: 1H of the CH$_2$ at 3 δ); 3.26 (s, 3H: NCH$_3$); 3.30 (t, J=12 Hz, 1H: other H of the CH$_2$ at 4 β); 3.36 (mt, 2H: NCH$_2$ of the ethyl); 3.54 (mt, 1H: other H of the CH$_2$ at 3 δ); 3.90 (limiting AB, 2H: NCH$_2$ allyl); 4.57 (dd, J=8 and 6 Hz, 1H: 3 α); 4.76 (broad dd, J=13 and 7.5 Hz, 1H: other H of the CH$_2$ at 5 ε); 4.84 (mt, 1H: 2 α); 4.89 (dd, J=10 and 1 Hz, 1H: 1 α); from 5.05 to 5.20 (mt, 3H: 4 α and =CH$_2$ of the allyl); 5.27 (broad d, J=6 Hz, 1H: 5 α); 5.83 (mt, 1H: CH= of the allyl); 5.88 (d, J=9.5 Hz, 1H: 6 α); 5.91 (mt, 1H: 1 β); 6.50 (d, J=10 Hz, 1H: NH at 2); 6.60 (d, J=8 Hz, 2H: aromatic H at 4 ε); 7.02 (d, J=8 Hz, 2H: aromatic H at 4 δ); from 7.10 to 7.35 (mt, 5H: aromatic H at 6); 7.47 (limiting AB, 2H: 1' H$_4$ and 1' H$_5$); 7.88 (dd, J=4 and 2 Hz, 1H: 1' H$_6$); 8.41 (d, J=10 Hz, 1H: NH at 1) 8.75 (d, J=9.5 Hz, 1H: NH at 6); 11.62 (s, 1H: OH).

The (R,S)-4-(allylethylamino)phenylalanine dihydrochloride may be prepared in the following way:

Working as in Example F, but starting with 4.54 g of diethyl 4-allylethylbenzylacetamidomalonate and 37.9 ml of 10N hydrochloric acid, and after evaporation, a solid is obtained which is dried under reduced pressure (2.7 kPa) at 40° C. 3.67 g of (R,S)-4-(allylethylamino)phenylalanine dihydrochloride are obtained in the form of a brown solid melting at about 130° C. (decomposition).

The diethyl 4-(allylethylamino)benzylacetamidomalonate may be prepared in the following way:

Working as in Example F, but starting with 8 g of diethyl 4-ethylaminobenzylacetamidomalonate, 4 ml of allyl bromide and 5.82 ml of 1,5-diazabicyclo-[4.3.0] non-5-ene in 50 ml of tetrahydrofuran, and after purification by flash chromatography (eluent: 90/10 CH$_2$Cl$_2$/EtOAc by volume), 5.6 g of a solid are obtained, which solid is recrystallized from 35 ml of cyclohexane. 5.43 g of diethyl 4-(allylethylamino)benzylacetamidomalonate are thus obtained in the form of a white solid melting at 86° C.

EXAMPLE V

Preparation of 4-ζ-(ethylpropylamino)de(4-ζ-dimethylamino)pristinamycin I$_A$

As described in Example F, a culture of the strain SP92::pVRC508 in production medium is produced on a 60-conical-flask scale with addition at 16 hours of 1 ml of a solution containing 20 g/l of (R,S)-4-(ethylpropylamino) phenylalanine dihydrochloride in 0.1N sodium hydroxide. After culturing for 40 hours, the 1.8 liters of broth obtained from the 60 flasks are extracted with 2 volumes of a mixture of 66% 100 mM phosphate buffer pH 2.9 and 34% acetonitrile and are then centrifuged. The supernatant is extracted with twice 0.5 volume of dichloromethane. The chloromethylene phases are washed with water and then pooled, dried over sodium sulphate and evaporated. The dry extract is taken up in 20 ml of dichloromethane and injected onto a column of silica (30 g) mounted in dichloromethane and eluted successively with levels of from 0 to 10% methanol in dichloromethane. The fractions containing the 4-ζ-(ethylpropylamino)de(4-ζ-dimethylamino)pristinamycin I$_A$ are pooled and evaporated. The dry residue is taken up in 7 ml of a 60% water and 40% acetonitrile mixture and is injected onto a Nucleosil 7μ C8 10×250 mm semi-preparative column (Macherey Nagel) eluted with a mixture of 63% 100 mM phosphate buffer pH 2.9 and 37% acetonitrile. The fractions containing the 4-ζ-(ethylpropylamino) de(4-ζ-dimethyl-amino)pristinamycin I$_A$ are pooled and extracted with one volume of dichloromethane. The organic phase is washed with water, dried over sodium sulphate and then evaporated. 16 mg of 4-ζ-(ethylpropylamino)de(4-ζ-dimethylamino)pristinamycin I$_A$ are obtained.

$^1$H NMR spectrum (400 MHz, CDCl$_3$, δ in ppm, ref. TMS): 0.67 (dd, J=16 and 6 Hz, 1H: 1H of the CH$_2$ at 5 β); 0.91 (t, J=7.5 Hz, 3H: CH$_3$ at 2 γ); 0.95 (t, J=7.5 Hz, 3H: CH$_3$ of the propyl); 1.14 (t, J=7 Hz, 3H: CH$_3$ of the ethyl); 1.15 (mt, 1H: 1H of the CH$_2$ at 3 β); 1.25 (mt, 1H: 1H of the CH$_2$ at 3 γ); 1.33 (d, J=7 Hz, 3H: CH$_3$ at 1 γ); from 1.45 to 1.65 (mt, 3H: other H of the CH$_2$ at 3 γ and CH$_2$ propyl); 1.63 and 1.75 (2 mts, 1H each: CH$_2$ at 2 β); 2.02 (mt, 1H: other H of the CH$_2$ at 3 β); 2.23 and 2.33 (mt and broad d respectively, J=16.5 Hz, 1H each: CH$_2$ at 5 δ); 2.37 (d, J=16 Hz, 1H: other H of the CH$_2$ at 5 β); 2.80 (dt, J=13 and 5 Hz, 1H: 1H of the CH$_2$ at 5 ε); 2.89 (dd, J=12 and 4 Hz, 1H: 1H of the CH$_2$ at 4 β); from 3.10 to 3.25 (mt, 3H: 1H of the CH$_2$ at 3 δ and NCH$_2$ of the propyl); 3.26 (s, 3H: NCH$_3$); 3.25 to 3.40 (mt, 2H: NCH$_2$ of the ethyl); 3.34 (t, J=12 Hz, 1H: other H of the CH$_2$ at 4 β); 3.54 (mt, 1H: other H of the CH$_2$ at 3 δ); 4.57 (dd, J=7.5 and 6 Hz, 1H: 3 α); 4.76 (broad dd, J=13 and 7.5 Hz, 1H: other H of the CH$_2$ at 5 ε); 4.84 (mt, 1H: 2 α); 4.89 (dd, J=10 and 1 Hz, 1H: 1 α); 5.21 (dd, J=12 and 4 Hz, 1H: 4 α); 5.28 (broad d, J=6 Hz, 1H: 5 α); 5.88 (d, J=9.5 Hz, 1H: 6 α); 5.91 (mt, 1H: 1 β); 6.48 (d, J=10 Hz, 1H: NH at 2); 6.60 (d, J=8 Hz, 2H: aromatic H at 4 ε); 7.03 (d, J=8 Hz, 2H: aromatic H at 4 δ); from 7.10 to 7.35 (mt, 5H: aromatic H at 6); 7.47 (limiting AB, 2H: 1' H$_4$ and 1' H$_5$); 7.89 (mt, 1H: 1' H$_6$); 8.42 (d, J=10 Hz, 1H: NH at 1); 8.76 (d, J=9.5 Hz, 1H: NH at 6); 11.62 (s, 1H: OH).

The (R,S)-4-(ethylpropylamino)phenylalanine dihydrochloride may be prepared in the following way:

Working as in Example F, but starting with 2.5 g of diethyl 4-ethylpropylaminobenzylacetamidomalonate and 21 ml of 10N hydrochloric acid, and after evaporation, a solid is obtained which is dried under reduced pressure (2.7 kPa) at 40° C. 2 g (97%) of (R,S)-4-(ethylpropylamino) phenylalanine dihydrochloride are obtained in the form of a white solid melting at about 147° C. (decomposition).

The diethyl 4-(ethylpropylamino) benzylacetamidomalonate may be prepared in the following way:

Working as in Example F, but starting with 10 g of diethyl 4-ethylaminobenzylacetamidomalonate, 5.6 ml of 1-iodopropane and 7.2 ml of 1,5-diazabicyclo-[4.3.0] non-5-ene in 70 ml of tetrahydrofuran, and after reacting for 36 hours followed by purification by flash chromatography (eluent: 97/3 CH$_2$Cl$_2$/MeOH by volume), 2.8 g of a solid are obtained, which solid is recrystallized from 26 ml of cyclohexane. 2.9 g of diethyl 4-(ethylpropylamino) benzylacetamidomalonate are thus obtained in the form of a white solid melting at 84–86° C.

SEPARATION AND PURIFICATION OF COMPONENTS OF THE B GROUP

EXAMPLE W 30 kg of crude pristinamycin [pristinamycin IA (PIA): 20.7%, pristinamycin IB (PIB): 3.9%, pristinamycin IC (PIC): 0.6%, pristinamycin ID (PID): 0.3%, pristinamycin IIB (PIIB): 8%, pristinamycin IIA (PIIA): 45%, pristinamycin IIF (PIIF): <0.5% (not assayed), pristinamycin IIG (PIIG): <0.5% (not assayed)] are suspended in 210 liters of ethyl acetate and stirred for 15 hours at room temperature. The suspension is filtered and the ethyl acetate filtrate collected is extracted with twice 20 liters of 1N sulphuric acid and then 20 liters of distilled water. The combined aqueous phases are washed with 6 times 15 liters of ethyl acetate and then adjusted to pH 7 by addition of 30 liters of 10% sodium bicarbonate solution and extracted with 3 times 30 liters of methylene chloride. The chloromethylene phases are combined and washed with 10 liters of distilled water. The methylene chloride is then distilled off and replaced by 50 liters of ethanol. The mixture is then treated at reflux with 0.8 kg of L3S charcoal for 30 minutes. After filtering and washing with twice 5 liters of ethanol, the mixture is cooled to 10° C. over 15 hours. After maintaining at 10° C. for one hour, the suspension is filtered and washed with 3 times 7 liters of ethanol. After drying the solid at 40° C. under reduced pressure, 5.7 kg of purified pristinamycin I (referred to hereinbelow as PI) are obtained.

Titre: 96.8% (PIA: 81.1%, PIB: 12%, PIC: 2.6%, PID: 1.1%); Yield of PIA: 74%

1500 g of purified PI are taken up in 9 liters of 1,2-dichloroethane, followed by addition of 1.5 equivalents of succinic anhydride and 0.015 equivalent of dimethylaminopyridine. The solution is maintained at 20° C. for 1 week and is then introduced onto a column containing 10 kg of silica (20–45 μm) [column height: 1 m; diameter: 20 cm]. The elution is carried out by percolating a 1,2-dichloroethane/methanol mixture through at a flow rate of 18 liters/hour for 6 hours; the percentage of methanol (containing 5% water) is increased from 0 to 4% during the chromatography. 47 2.4-liter fractions are recovered.

Fractions 5 to 15 are combined and the 1,2-dichloroethane is evaporated off and replaced with 5 liters of ethanol. After crystallization, 365 g of PIA with a titre of 99.8% are obtained.

PREPARATION OF CRUDE COMPONENTS OF THE A GROUP

EXAMPLE X 500 g of crude pristinamycin [pristinamycin IA (PIA): 20.7%, pristinamycin IB (PIB): 3.9%, pristinamycin IC (PIC): 0.6%, pristinamycin ID (PID): 0.3%, pristinamycin IIB (PIIB): 8%, pristinamycin IIA (PIIA ): 45%] are dissolved in 50 liters of methyl isobutyl ketone. This solution is extracted 5 times with an aqueous phase composed of 2.5 liters of water and 2.5 liters of 1N sulphuric acid, and is then washed with 3 times 10 liters of water. The methyl isobutyl ketone is then treated with 7.5 liters of aqueous sodium hydrogen carbonate solution at a concentration of 35 g/liter and then washed with 5 liters of water. Each time, the aqueous phase is mixed with the organic phase and separated out after settling has taken place.

The organic phase obtained is placed in contact with 750 g of alumina, filtered, concentrated to a volume of about 4 liters and taken up in 5 volumes of hexane. The precipitate obtained is filtered off and dried. 300 g of product are obtained, which product is suspended in 1 liter of isopropanol. After stirring at 55° C. for 45 minutes, the suspension is filtered at 4° C. The filtration mother liquors are concentrated to dryness and taken up in 500 cm³ of methyl isobutyl ketone, into which are poured 5 volumes of hexane. The precipitate is filtered off, washed with hexane and dried at 40° C. under reduced pressure. 69 g of crude PIIB containing 36% PIIB, 6% PIIA and no longer containing PIA are obtained.

EXAMPLE Y 60 g of crude PIIB obtained as above in EXAMPLE P are purified in several operations, by chromatography on a column of Nucleosil 5C8® (column diameter: 5 cm, height: 30 cm) through which a 60/40 water/acetonitrile eluent is percolated. 250 mg of pristinamycin IIF (PIIF) are thus obtained.

The present invention also relates to pharmaceutical compositions which can be used in human or veterinary medicine and which contain as active product the novel purified streptogramin combination comprising at least one component of the streptogramin B group defined by the general formula (I) co-crystallized with at least one component of the A group of general formula (II), in the pure state or in the presence of one or more compatible and pharmaceutically acceptable diluents or adjuvants. These compositions may be used orally or topically.

As compositions for oral administration, tablets, hard gelatin capsules, pills, powders, lyophilizates or granules may be used. In these compositions, the active product according to the invention may be mixed with one or more inert diluents or adjuvants such as sucrose, lactose or starch. These compositions can also comprise substances other than diluents, for example a lubricant such as magnesium stearate.

The compositions for topical administration can be, for example, creams, ointments or lotions.

In human or veterinary therapy, the compositions according to the invention are especially useful in the treatment of infections of bacterial origin, in particular severe infections caused by Gram-positive cocci: staphylococcal infections (in particular infections caused by methicillin-resistant staphylococci), streptococcal infections (in particular against penicillin- and macrolide-resistant pneumococci); they are also especially useful in the treatment of infections caused by Hemophilus, *Moraxella catarrhalis, Neisseria gonorrhoeae, Chlamydia trachomatis, Mycoplasma hominis, Mycoplasma pneumoniae* and *Ureaplasma urealyticum*.

The compositions according to the invention may be employed, in particular, in the treatment of upper and lower respiratory infections (for example treatment of pulmonary infections), in the treatment of skin infections, in the long-term treatment of bone or joint infections, in the treatment or prophylaxis of endocarditis in dental and urinary surgery, in the treatment of sexually transmitted diseases and also in the treatment of the opportunistic bacterial and parasitic infections occurring in AIDS and for prophylaxis of the risk of Staphylococcus in immunosuppressed patients.

Generally speaking, the doctor will determine the dosage he considers most suitable in accordance with the age, weight, degree of infection and other factors distinctive to the subject who is to be treated. Generally, the doses are between 0.4 and 3.5 g of active product taken in 2 or 3 doses daily via the oral route for an adult.

The examples which follow, given without implied limitation, illustrate some compositions according to the invention:

EXAMPLE A

Opaque hard gelatin capsules containing a 250 mg dose of the co-crystallized 4-ε-chloropristinamycin $I_A$/pristinamycin IIB combination are prepared according to the usual techniques.

EXAMPLE B

Opaque hard gelatin capsules containing a 250 mg dose of the co-crystallized de(4-ζ-dimethylamino)-4-ε-methoxypristinamcyin $I_A$/pristinamycin IIB combination are prepared according to the usual techniques.

What is claimed is:
1. A cocrystallizate comprising at least one component from the streptogramin B group defined by the formula (I):

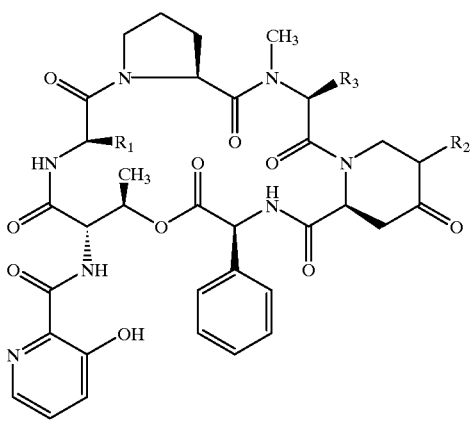
(I)

in which:
R$_1$ represents a methyl or ethyl radical,
R$_2$ represents a hydrogen atom or a hydroxyl radical, and
R$_3$ represents a substituted benzyl radical of formula (III):

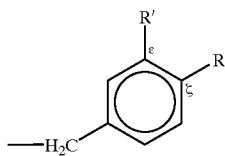
(III)

in which:
(1) R$_2$ in formula (1) is hydrogen, and R represents: NR$_4$R$_5$ wherein one of R$_4$ and R$_5$ is a hydrogen atom or a methyl radical and the other is a methyl radical, and R' is a chlorine or bromine atom; or an alkenyl radical containing 3 to 5 carbon atoms when R$_4$ and R$_5$ are both methyl radicals; or, alternatively,
(2) R represents a hydrogen atom and R' represents a halogen atom, an alkylamino or dialkylamino radical an ether oxide residue OR$^0$ where R$^0$ is a methyl group, an ethyl group which is optionally substituted with a chlorine atom, an allyl group, or a trifluoromethyl group, an alkylthio radical, an alkyl radical containing 1 to 3 carbon atoms in a straight or branched chain or a trihalomethyl radical; or, alternatively,
(3) R represents a halogen atom, an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an alkenylalkylamino radical in which the alkenyl part contains 3 or 4 carbon atoms and the alkyl part is defined as above, a dialkenylamino radical in which the alkenyl parts are defined as above, an alkylcycloalkylmethylamino radical in which the alkyl part is defined as above and the cycloalkyl part contains 3 or 4 carbon atoms, an ether oxide residue OR$^0$ where R$^0$ is a methyl group, an ethyl group which is optionally substituted with a chlorine atom, an allyl group, or a trifluoromethyl group, an alkylthio radical, an alkylthiomethyl radical, an alkyl radical containing 1 to 6 carbon atoms in a straight or branched chain, an aryl radical or a trihalomethyl radical, and R' is a hydrogen atom; or, alternatively,
(4) R represents a halogen atom, an amino, alkylamino or dialkylamino radical, an ether oxide residue OR$^0$ where R$^0$ is a methyl group, an ethyl group which is optionally substituted with a chlorine atom, an allyl group, or a trifluoromethyl group, an alkylthio radical, an alkyl radical containing 1 to 6 carbon atoms in a straight or branched chain or a trihalomethyl radical and R' represents a halogen atom, an alkylamino or dialkylamino radical, an ether oxide residue OR$^0$ where R$^0$ is a methyl group, an ethyl group which is optionally substituted with a chlorine atom, an allyl group, or a trifluoromethyl group, or an alkylthio or alkyl radical containing 1 to 3 carbon atoms in a straight or branched chain;

and at least one component of the streptogramin A group, of formula (II):

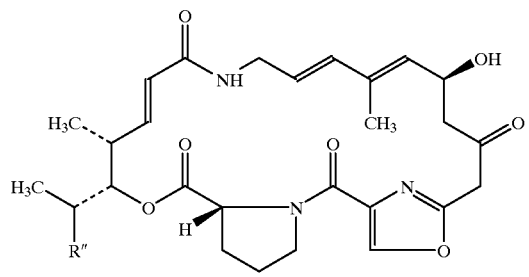
(II)

in which R" is a hydrogen atom or a methyl or ethyl radical; with the proviso that, except where specifically mentioned, the alkyl radicals are straight or branched and contain 1 to 4 carbon atoms.

2. A cocrystallizate according to claim 1, which comprises at least one component of the streptogramin B group defined by the formula (I)) in claim 1, in which:
R$_1$ and R$_2$ are defined as in claim 1, and R$_3$ represents a substituted benzyl radical of formula (III):

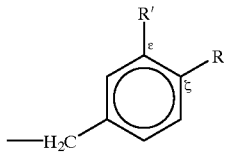
(III)

in which:
(1) R$_2$ is hydrogen, and R represents:
NR$_4$R$_5$ for which one of R$_4$ and R$_5$ is a hydrogen atom or a methyl radical and the other is a methyl radical and R' is a chlorine or bromine atom; or an alkenyl radical containing 3 to 5 carbon atoms when R$_4$ and R$_5$ are both methyl radicals; or, alternatively,
(2) R represents a hydrogen atom and R' represents an alkylamino or dialkylamino radical, an ether oxide residue OR$^0$ where R$^0$ is a methyl group, an ethyl group which is optionally substituted with a chlorine atom, an allyl group, or a trifluoromethyl group, or an alkylthio radical; or, alternatively, (3) R represents an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an alkenylalkylamino radical in which the alkenyl part contains 3 or 4 carbon atoms and the alkyl part is defined as above, an ether oxide residue $OR^O$ where $R^O$ is a methyl group, an ethyl group which is optionally substituted with a chlorine atom, an allyl group, or a trifluoromethyl group, an alkylthio radical, an alkyl radical containing 1 to 6 carbon atoms in a straight or branched chain or a trihalomethyl radical, and R' is a hydrogen atom; or, alternatively, (4) R represents an alkyl radical containing 1 to 6 carbon atoms in a straight or branched chain and R' represents a halogen atom;

and at least one component of the streptogramin A group as defined in claim 1, with the proviso that, except where specifically mentioned, the alkyl radicals are straight or branched and contain 1 to 4 carbon atoms.

3. A cocrystallizate according to claim 1, in which
$R_1$ is an ethyl radical,
$R_2$ is a hydrogen atom, and
$R_3$ represents a substituted benzyl radical of formula (III):

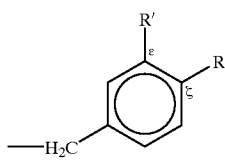

in which:
(1) $R_2$ is hydrogen, and R represents:
   $NR_4R_5$ wherein one of $R_4$ and $R_5$ is a hydrogen atom or a methyl radical and the other is a methyl radical, and R' is a chlorine or bromine atom; or an allyl radical when $R_4$ and $R_5$ are both methyl radicals; or, alternatively, (2) R represents a hydrogen atom and R' represents an alkylamino or dialkylamino radical, a methoxy, ethoxy, allyloxy or trifluoromethoxy radical or an alkylthio radical; or alternatively, (3) R represents an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an alkenylalkylamino radical in which the alkenyl part contains 3 or 4 carbon atoms and the alkyl part is defined as above, a methoxy, ethoxy, allyloxy or trifluoromethoxy radical, an alkylthio radical, an alkyl radical containing 1 to 6 carbon atoms in a straight or branched chain or a trifluoromethyl radical, and R' is a hydrogen atom; or alternatively, (4) R represents a an alkyl radical containing 1 to 6 carbon atoms in a straight or branched chain and R' represents a halogen atom and at least one component of the streptogramin A group as defined in claim 1;

with the proviso that, except where specifically mentioned, the alkyl radicals are straight or branched and contain 1 to 4 carbon atoms.

4. A cocrystallizate according to claim 1, said cocrystallizate comprising at least one component of the streptogramin B group as defined in claim 1 and at least one component of the streptogramin A group as defined in claim 1, in a molar ratio of about ½.

5. A process for preparing a co-crystallizate, which process comprises co-crystallizing at least one component of the streptogramin A group as defined in claim 1 with at least one component of the streptogramin B group as defined in claim 1.

6. A pharmaceutical composition comprising a pharmaceutically effective amount of a cocrystallizate according to claim 1 together with a compatible and pharmaceutically acceptable diluent or adjuvant.

7. An oral antibiotic product comprising a cocrystallizate together with a compatible and pharmaceutically acceptable diluent or adjuvant, said cocrystallizate comprising (I):

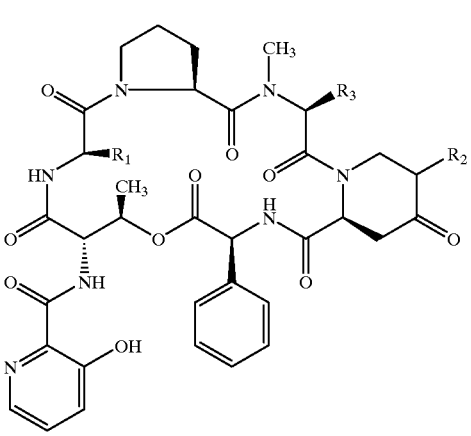

in which:
$R_1$ represents a methyl or ethyl radical,
$R_2$ represents a hydrogen atom or a hydroxyl radical, and
$R_3$ represents a substituted benzyl radical of formula (III):

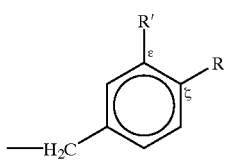

in which:
(1) $R_2$ in formula (1) is hydrogen, and R represents:
   $NR_4R_5$ wherein one of $R_4$ and $R_5$ is a hydrogen atom or a methyl radical and the other is a methyl radical, and R' is a chlorine or bromine atom;
   or an alkenyl radical containing 3 to 5 carbon atoms when $R_4$ and $R_5$ are both methyl radicals; or, alternatively, (2) R represents a hydrogen atom and R' represents a halogen atom, an alkylamino or dialkylamino radical, an ether oxide residue $OR^O$ where $R^O$ is a methyl group, an ethyl group which is optionally substituted with a chlorine atom, an allyl group, or a trifluoromethyl group, an alkylthio radical, an alkyl radical containing 1 to 3 carbon atoms in a straight or branched chain or a trihalomethyl radical; or, alternatively, (3) R represents a halogen atom, an alkylamino radical containing 2 to 4 carbon atoms in a straight or branched chain, a dialkylamino radical in which the alkyl parts are identical or different and contain 2 to 4 carbon atoms in a straight or branched chain or a methylethylamino radical, a pyrrolidino radical, an alkenylalkylamino radical in which the alkenyl part contains 3 or 4 carbon atoms and the alkyl part is defined as above, a dialkenylamino radical in which the alkenyl parts are defined as above, an alkylcycloalkylmethylamino radical in which the alkyl part is defined as above and the cycloalkyl part contains 3 or 4 carbon atoms, an ether oxide residue OR$^0$ where R$^0$ is a methyl group, an ethyl group which is optionally substituted with a chlorine atom, an allyl group or a trifluoromethyl group, an alkylthio radical, an alkylthiomethyl radical, an alkyl radical containing 1 to 6 carbon atoms in a straight or branched chain, an aryl radical or a trihalomethyl radical, and R' is a hydrogen atom; or, alternatively, (4) R represents a halogen atom, an amino, alkylamino or dialkylamino radical, an ether oxide residue OR$^0$ where R$^0$ is a methyl group, an ethyl group which is optionally substituted with a chlorine atom, an allyl group, or a trifluoromethyl group, an alkylthio radical, an alkyl radical containing 1 to 6 carbon atoms in a straight or branched chain or a trihalomethyl radical and R' represents a halogen atom, an alkylamino or dialkylamino radical, an alkoxy radical, an allylalkoxy radical, a halogenated alkoxy radical, or an alkylthio or alkyl radical containing 1 to 3 carbon atoms in a straight or branched chain;

and at least one component of the streptogramin A group, of formula (II):

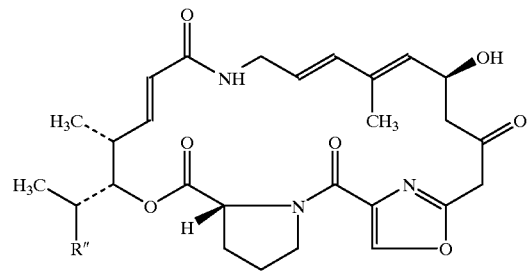

in which R" is a hydrogen atom or a methyl or ethyl radical;

with the proviso that, except where specifically mentioned, the alkyl radicals are straight or branched and contain 1 to 4 carbon atoms.

* * * * *

UNITED STATES PATENT AND TRADEMARK OFFICE
CERTIFICATE OF CORRECTION

PATENT NO. : 6,384,014 B1
DATED : May 7, 2002
INVENTOR(S) : Pascal Anger et al.

It is certified that error appears in the above-identified patent and that said Letters Patent is hereby corrected as shown below:

Column 41,
Line 43, after "radical", insert -- , --.

Column 42,
Line 41, "formula (I))" should read -- formula(I) --.

Column 43,
Line 60, before "an", delete "a".

Column 44,
Line 13, after "claim 1", insert -- , --.
Line 52, "formula (1)" should read -- formula (I) --.

Signed and Sealed this

Twenty-fifth Day of February, 2003

JAMES E. ROGAN
*Director of the United States Patent and Trademark Office*